US012259231B2

(12) United States Patent
Pesach et al.

(10) Patent No.: US 12,259,231 B2
(45) Date of Patent: Mar. 25, 2025

(54) INTRAORAL SCANNER

(71) Applicant: Dentlytec G.P.L. LTD., Hod Hasharon (IL)

(72) Inventors: Benny Pesach, Rosh Haayin (IL); Amitai Reuvenny, Kfar-Saba (IL)

(73) Assignee: DENTLYTEC G.P.L. LTD., Hod Hasharon (IL)

( * ) Notice: Subject to any disclaimer, the term of this patent is extended or adjusted under 35 U.S.C. 154(b) by 0 days.

(21) Appl. No.: 18/601,963

(22) Filed: Mar. 11, 2024

(65) Prior Publication Data

US 2025/0044079 A1 Feb. 6, 2025

Related U.S. Application Data

(63) Continuation of application No. 17/211,640, filed on Mar. 24, 2021, now Pat. No. 12,025,430, which is a
(Continued)

(51) Int. Cl.
*A61C 17/20* (2006.01)
*A61B 1/00* (2006.01)
(Continued)

(52) U.S. Cl.
CPC ........ *G01B 11/25* (2013.01); *A61B 1/000094* (2022.02); *A61B 1/00194* (2022.02);
(Continued)

(58) Field of Classification Search
CPC .............. G01B 11/25; A61B 1/000094; A61B 1/00194; A61B 1/045; A61B 1/0605;
(Continued)

(56) References Cited

U.S. PATENT DOCUMENTS 3,634,938 A 1/1972 Hutchinson
4,279,598 A 7/1981 Scheicher
(Continued)

FOREIGN PATENT DOCUMENTS

CN 101677757 A 3/2010
EP 1901033 A1 3/2008
(Continued)

OTHER PUBLICATIONS

Applicant-Initiated Interview Summary Dated Aug. 2, 2017 From the US Patent and Trademark Office Re. U.S. Appl. No. 15/115,196. (3 pages).
(Continued)

*Primary Examiner* — Howard D Brown, Jr.
(74) *Attorney, Agent, or Firm* — COOLEY LLP

(57) ABSTRACT

A method for intraoral scanning, including introducing an intraoral scanner (IOS) head into an oral cavity, acquiring an image of a field of view (FOV), processing the acquired FOV image and adjusting at least one image acquisition parameter based on said processing, and an intraoral scanner (IOS) including an IOS head including at least one imager imaging a field of view (FOV), at least on light emitter that illuminates said FOV and circuitry that controls said imager and/or said light emitter.

20 Claims, 13 Drawing Sheets

Related U.S. Application Data continuation of application No. 16/071,058, filed as application No. PCT/IL2017/050072 on Jan. 18, 2017, now Pat. No. 10,966,614, which is a continuation-in-part of application No. PCT/IL2016/050058, filed on Jan. 18, 2016.

(60) Provisional application No. 62/364,681, filed on Jul. 20, 2016, provisional application No. 62/104,835, filed on Jan. 18, 2015.

(51) Int. Cl.
| | |
|---|---|
| *A61B 1/045* | (2006.01) |
| *A61B 1/06* | (2006.01) |
| *A61B 5/00* | (2006.01) |
| *G01B 11/25* | (2006.01) |
| *G06T 7/00* | (2017.01) |
| *G06T 7/11* | (2017.01) |
| *A61B 1/24* | (2006.01) |

(52) U.S. Cl.
CPC ............ *A61B 1/045* (2013.01); *A61B 1/0605* (2022.02); *A61B 1/0655* (2022.02); *A61B 5/0088* (2013.01); *G06T 7/0012* (2013.01); *G06T 7/11* (2017.01); *A61B 1/0607* (2013.01); *A61B 1/24* (2013.01); *A61B 2562/0233* (2013.01)

(58) Field of Classification Search
CPC ... A61B 1/0655; A61B 5/0088; A61B 1/0607; A61B 1/24; A61B 2562/0233; A61B 5/682; A61B 1/0676; G06T 7/0012; G06T 7/11; A61C 1/088; A61C 19/04; A61C 9/0053

See application file for complete search history.

(56) References Cited

U.S. PATENT DOCUMENTS

| | | |
|---|---|---|
| 4,478,580 A | 10/1984 | Barrut |
| 4,571,180 A | 2/1986 | Kulick |
| 4,665,621 A | 5/1987 | Ackerman et al. |
| 4,764,114 A | 8/1988 | Jeffcoat et al. |
| 4,790,751 A | 12/1988 | Reinhardt et al. |
| 4,823,809 A | 4/1989 | Gott, Jr. et al. |
| 4,873,651 A | 10/1989 | Raviv |
| 4,883,425 A | 11/1989 | Zimble |
| 4,935,635 A | 6/1990 | O'Harra |
| 5,049,070 A | 9/1991 | Ademovic |
| 5,051,823 A | 9/1991 | Cooper et al. |
| 5,176,687 A | 1/1993 | Hasson et al. |
| 5,178,536 A | 1/1993 | Werly et al. |
| 5,178,537 A | 1/1993 | Currie |
| 5,190,456 A | 3/1993 | Hasegawa |
| 5,215,521 A | 6/1993 | Cochran et al. |
| 5,224,049 A | 6/1993 | Mushabac |
| 5,230,621 A | 7/1993 | Jacoby |
| 5,244,387 A | 9/1993 | Fuierer |
| 5,257,184 A | 10/1993 | Mushabac |
| 5,313,053 A | 5/1994 | Koenck et al. |
| 5,318,442 A | 6/1994 | Jeffcoat et al. |
| 5,320,462 A | 6/1994 | Johansson et al. |
| 5,368,597 A | 11/1994 | Pagedas |
| 5,372,502 A | 12/1994 | Massen et al. |
| 5,423,677 A | 6/1995 | Brattesani |
| 5,435,722 A | 7/1995 | Mandell |
| 5,618,296 A | 4/1997 | Sorensen et al. |
| 5,634,790 A | 6/1997 | Pathmanabhan et al. |
| 5,743,731 A | 4/1998 | Lares et al. |
| 5,850,289 A | 12/1998 | Fowler et al. |
| 5,862,559 A | 1/1999 | Hunter |
| 5,897,509 A | 4/1999 | Toda et al. |
| 5,919,129 A | 7/1999 | Vandre |
| 5,944,523 A | 8/1999 | Badoz |
| 5,969,321 A | 10/1999 | Danielson et al. |
| 5,993,209 A | 11/1999 | Matoba et al. |
| 6,000,939 A | 12/1999 | Ray et al. |
| 6,007,333 A | 12/1999 | Callan et al. |
| 6,116,899 A | 9/2000 | Takeuchi |
| 6,142,936 A | 11/2000 | Beane et al. |
| 6,179,611 B1 | 1/2001 | Everett et al. |
| 6,241,519 B1 | 6/2001 | Sedelmayer |
| 6,257,889 B1 | 7/2001 | Boston |
| 6,276,934 B1 | 8/2001 | Rakocz |
| 6,309,219 B1 | 10/2001 | Robert |
| 6,406,440 B1 | 6/2002 | Stefanchik |
| 6,468,079 B1 | 10/2002 | Fischer et al. |
| 6,819,318 B1 | 11/2004 | Geng |
| 6,885,464 B1 | 4/2005 | Pfeiffer et al. |
| 7,041,056 B2 | 5/2006 | Deslauriers et al. |
| 7,056,329 B2 | 6/2006 | Kerr |
| 7,346,417 B2 | 3/2008 | Lüth et al. |
| 7,494,338 B2 | 2/2009 | Durbin et al. |
| 7,625,335 B2 | 12/2009 | Deichmann et al. |
| 7,668,583 B2 | 2/2010 | Fegert et al. |
| 7,813,591 B2 | 10/2010 | Paley et al. |
| 8,280,152 B2 | 10/2012 | Thiel et al. |
| 8,371,848 B2 | 2/2013 | Okawa et al. |
| 8,439,682 B1 | 5/2013 | Heath et al. |
| 8,744,194 B2 | 6/2014 | Kawasaki et al. |
| 8,936,470 B2 | 1/2015 | Pruckner et al. |
| 9,137,511 B1 | 9/2015 | LeGrand, III et al. |
| 9,179,987 B2 | 11/2015 | Goodacre |
| 9,463,081 B2 | 10/2016 | Urakabe |
| 9,522,054 B2 | 12/2016 | Kim et al. |
| 9,603,675 B2 | 3/2017 | Pruckner |
| 9,918,805 B2 | 3/2018 | Pruckner |
| 10,136,970 B2 | 11/2018 | Pesach |
| 10,299,880 B2 | 5/2019 | Ramirez Luna et al. |
| 10,470,846 B2 | 11/2019 | Kopelman et al. |
| 10,695,150 B2 | 6/2020 | Kopelman et al. |
| 12,025,430 B2 | 7/2024 | Pesach et al. |
| 2002/0037490 A1 | 3/2002 | Oyamada et al. |
| 2002/0103420 A1 | 8/2002 | Coleman et al. |
| 2002/0133096 A1 | 9/2002 | Toda et al. |
| 2004/0041996 A1 | 3/2004 | Abe |
| 2004/0087937 A1 | 5/2004 | Eggers et al. |
| 2004/0097792 A1 | 5/2004 | Moll et al. |
| 2004/0106868 A1 | 6/2004 | Liew et al. |
| 2004/0117052 A1 | 6/2004 | Geng |
| 2004/0158261 A1 | 8/2004 | Vu |
| 2004/0191725 A1 | 9/2004 | Szymaitis |
| 2005/0116673 A1 | 6/2005 | Carl et al. |
| 2006/0085005 A1 | 4/2006 | Kenealy et al. |
| 2006/0154198 A1 | 7/2006 | Durbin et al. |
| 2007/0037125 A1 | 2/2007 | Maev et al. |
| 2007/0042315 A1 | 2/2007 | Boutoussov et al. |
| 2007/0064242 A1 | 3/2007 | Childers |
| 2007/0065782 A1 | 3/2007 | Maschke |
| 2007/0172112 A1 | 7/2007 | Paley et al. |
| 2007/0225744 A1 | 9/2007 | Nobles et al. |
| 2007/0260231 A1 | 11/2007 | Rose et al. |
| 2008/0002011 A1 | 1/2008 | Mizutani et al. |
| 2008/0002869 A1 | 1/2008 | Scharlack et al. |
| 2008/0038688 A1 | 2/2008 | Kopelman et al. |
| 2008/0145817 A1 | 6/2008 | Brennan et al. |
| 2008/0160477 A1 | 7/2008 | Stookey et al. |
| 2008/0201101 A1 | 8/2008 | Hebert et al. |
| 2008/0234579 A1 | 9/2008 | Halevy-Politch et al. |
| 2008/0255498 A1 | 10/2008 | Houle |
| 2008/0261165 A1 | 10/2008 | Steingart et al. |
| 2009/0017416 A1 | 1/2009 | Nguyen et al. |
| 2009/0043314 A1 | 2/2009 | Sevensson et al. |
| 2009/0061383 A1 | 3/2009 | Kang |
| 2009/0087050 A1 | 4/2009 | Gandyra |
| 2009/0306506 A1 | 12/2009 | Heger et al. |
| 2009/0326383 A1 | 12/2009 | Barnes et al. |
| 2010/0047733 A1 | 2/2010 | Nahlieli |
| 2010/0092908 A1 | 4/2010 | Rothenwaender et al. |
| 2010/0189341 A1 | 7/2010 | Oota et al. |
| 2010/0238279 A1 | 9/2010 | Thoms et al. |
| 2010/0239136 A1 | 9/2010 | Gandyra et al. |

(56) References Cited

U.S. PATENT DOCUMENTS

| | | |
|---|---|---|
| 2010/0239996 A1 | 9/2010 | Ertl |
| 2010/0268069 A1 | 10/2010 | Liang |
| 2010/0268071 A1 | 10/2010 | Kim |
| 2010/0303341 A1 | 12/2010 | Häusler |
| 2010/0305435 A1 | 12/2010 | Magill |
| 2011/0190781 A1 | 8/2011 | Collier et al. |
| 2011/0301419 A1 | 12/2011 | Craft et al. |
| 2012/0015329 A1 | 1/2012 | Gross et al. |
| 2012/0040305 A1 | 2/2012 | Karazivan et al. |
| 2012/0046536 A1 | 2/2012 | Cheung et al. |
| 2012/0062557 A1 | 3/2012 | Dillon et al. |
| 2012/0097002 A1 | 4/2012 | Thiedig |
| 2012/0179281 A1 | 7/2012 | Steingart et al. |
| 2012/0189182 A1 | 7/2012 | Liang et al. |
| 2012/0270177 A1 | 10/2012 | Nakashima et al. |
| 2012/0271176 A1 | 10/2012 | Moghaddam et al. |
| 2013/0000666 A1 | 1/2013 | Hu |
| 2013/0017507 A1 | 1/2013 | Moffson et al. |
| 2013/0027515 A1 | 1/2013 | Vinther et al. |
| 2013/0060144 A1 | 3/2013 | Culjat et al. |
| 2013/0188012 A1 | 7/2013 | Bellis et al. |
| 2013/0209953 A1 | 8/2013 | Arlinsky et al. |
| 2013/0253278 A1 | 9/2013 | Smith |
| 2013/0273492 A1 | 10/2013 | Suttin, Sr. et al. |
| 2014/0066784 A1 | 3/2014 | Yokota |
| 2014/0093835 A1 | 4/2014 | Levin |
| 2014/0111616 A1 | 4/2014 | Blayvas |
| 2014/0120492 A1 | 5/2014 | Ioannidis et al. |
| 2014/0120493 A1 | 5/2014 | Levin |
| 2014/0146142 A1 | 5/2014 | Duret et al. |
| 2014/0178832 A1 | 6/2014 | Choi et al. |
| 2014/0194696 A1 | 7/2014 | Fischvogt |
| 2014/0199650 A1 | 7/2014 | Moffson et al. |
| 2014/0212832 A1* | 7/2014 | Fisker ................. A61B 5/0062 433/29 |
| 2014/0221819 A1 | 8/2014 | Sarment |
| 2014/0248577 A1 | 9/2014 | Tahmasebi et al. |
| 2014/0276055 A1 | 9/2014 | Barthe et al. |
| 2014/0309523 A1 | 10/2014 | Daon et al. |
| 2014/0330285 A1 | 11/2014 | Rosenblatt et al. |
| 2014/0343395 A1 | 11/2014 | Choi et al. |
| 2015/0015701 A1 | 1/2015 | Yu |
| 2015/0118638 A1 | 4/2015 | Cowburn |
| 2015/0182299 A1 | 7/2015 | Koubi et al. |
| 2015/0223910 A1 | 8/2015 | Pruckner |
| 2015/0223916 A1 | 8/2015 | Kim et al. |
| 2015/0229911 A1 | 8/2015 | Ge et al. |
| 2015/0297254 A1 | 10/2015 | Sullivan et al. |
| 2015/0348320 A1 | 12/2015 | Pesach et al. |
| 2016/0120615 A1 | 5/2016 | Scurtescu |
| 2016/0163115 A1 | 6/2016 | Furst |
| 2016/0259515 A1 | 9/2016 | Sabina et al. |
| 2016/0262856 A1 | 9/2016 | Atiya et al. |
| 2016/0270878 A1 | 9/2016 | Fulton, III |
| 2016/0338682 A1 | 11/2016 | Hoyte et al. |
| 2016/0338803 A1 | 11/2016 | Pesach |
| 2017/0007377 A1* | 1/2017 | Pesach ................ H04N 23/00 |
| 2017/0173262 A1* | 6/2017 | Veltz ................ G16H 20/17 |
| 2017/0202483 A1 | 7/2017 | Sorimoto et al. |
| 2017/0215997 A1* | 8/2017 | Martin ................ A61B 5/6835 |
| 2018/0318051 A1 | 11/2018 | Lu et al. |
| 2018/0360481 A1 | 12/2018 | Bonadio et al. |
| 2019/0125297 A1 | 5/2019 | Chan et al. |
| 2019/0192262 A1 | 6/2019 | Pesach |
| 2019/0247033 A1 | 8/2019 | Yaari |
| 2019/0262098 A1 | 8/2019 | Pesach et al. |
| 2019/0343598 A1* | 11/2019 | Knobel ................ A61C 1/084 |
| 2020/0060550 A1 | 2/2020 | Pesach et al. |
| 2020/0155274 A1 | 5/2020 | Pimenov et al. |
| 2020/0155285 A1 | 5/2020 | Pesach et al. |
| 2020/0268410 A1 | 8/2020 | Yaari et al. |
| 2021/0321872 A1* | 10/2021 | Saphier ................ G06V 20/64 |
| 2022/0071737 A1 | 3/2022 | Pesach et al. |
| 2022/0151756 A1* | 5/2022 | Pesach ................ A61B 5/4547 |
| 2023/0181295 A1 | 6/2023 | Pesach et al. |
| 2023/0285124 A1 | 9/2023 | Pesach et al. |

FOREIGN PATENT DOCUMENTS

| | | |
|---|---|---|
| EP | 2165674 A1 | 3/2010 |
| EP | 2630929 A2 | 8/2013 |
| ES | 2115544 A1 | 6/1998 |
| FR | 2692773 A1 | 12/1993 |
| GB | 2495522 A | 4/2013 |
| JP | S635742 A | 1/1988 |
| JP | H07155297 A | 6/1995 |
| JP | H10165425 A | 6/1998 |
| JP | H10262996 A | 10/1998 |
| JP | H11192207 A | 7/1999 |
| JP | 2002125927 A | 5/2002 |
| JP | 2003325451 A | 11/2003 |
| JP | 2006102497 A | 4/2006 |
| JP | 2007152004 A | 6/2007 |
| JP | 2007296249 A | 11/2007 |
| JP | 2009268614 A | 11/2009 |
| JP | 2010104652 A | 5/2010 |
| JP | 2012016573 A | 1/2012 |
| JP | 5016311 B2 | 9/2012 |
| JP | 2014236957 A | 12/2014 |
| JP | 5661255 B2 | 1/2015 |
| KR | 101782740 B1 | 9/2017 |
| WO | WO-9806352 A1 | 2/1998 |
| WO | WO-2005104959 A1 | 11/2005 |
| WO | WO-2007063980 A1 | 6/2007 |
| WO | WO-2008013181 A1 | 1/2008 |
| WO | WO-2014020247 A1 | 2/2014 |
| WO | WO-2014102779 A2 | 7/2014 |
| WO | WO-2015028646 A1 | 3/2015 |
| WO | WO-2015107520 A1 | 7/2015 |
| WO | WO-2016028789 A2 | 2/2016 |
| WO | WO-2016064617 A1 | 4/2016 |
| WO | WO-2016110855 A1 | 7/2016 |
| WO | WO-2016113745 A1 | 7/2016 |
| WO | WO-2016178212 A1 | 11/2016 |
| WO | WO-2017125926 A2 | 7/2017 |
| WO | WO-2017216803 A1 | 12/2017 |
| WO | WO-2018047180 A1 | 3/2018 |
| WO | WO-2019008586 A1 | 1/2019 |
| WO | WO-2019021285 A1 | 1/2019 |
| WO | WO-2019049152 A1 | 3/2019 |
| WO | WO-2020144692 A2 | 7/2020 |

OTHER PUBLICATIONS

Bouguet et al. "3D Photography Using Shadows in Dual-Space Geometry", The International Journal of Computer Vision, 35(2): 129-149, Nov./Dec. 1999.

Communication Pursuant to Article 94(3) EPC Dated Jul. 1, 2022 From the European Patent Office Re. Application No. 18837606.5. (4 Pages).

Communication Pursuant to Article 94(3) EPC Dated Oct. 4, 2023 From the European Patent Office Re. Application No. 18837606.5 (4 Pages).

Communication Pursuant to Article 94(3) EPC Dated Oct. 5, 2021 From the European Patent Office Re. Application No. 18759184.7. (6 Pages).

Communication Pursuant to Article 94(3) EPC Dated Oct. 7, 2020 From the European Patent Office Re. Application No. 17780530.6. (5 Pages).

Communication Pursuant to Article 94(3) EPC Dated Aug. 10, 2017 From the European Patent Office Re. Application No. 13830124.7. (6 Pages).

Communication Pursuant to Article 94(3) EPC Dated Nov. 16, 2021 From the European Patent Office Re. Application No. 17707964.7. (4 Pages).

Communication Pursuant to Article 94(3) EPC Dated Nov. 19, 2018 From the European Patent Office Re. Application No. 13830124.7. (8 Pages).

(56) References Cited

OTHER PUBLICATIONS

Communication Pursuant to Article 94(3) EPC Dated Nov. 19, 2020 From the European Patent Office Re. Application No. 13830124.7. (6 Pages).
Communication Pursuant to Article 94(3) EPC Dated Jul. 21, 2023 from the European Patent Office Re: Application No. 18837606.5, 5 Pages.
Communication Pursuant to Article 94(3) EPC Dated Nov. 21, 2023 From the European Patent Office Re. Application No. 21200149.9 (5 Pages).
Communication Pursuant to Article 94(3) EPC Dated Apr. 25, 2024 From the European Patent Office Re. Application No. 22207979.0 (5 Pages).
Communication Pursuant to Article 94(3) EPC Dated Jan. 29, 2021 From the European Patent Office Re. Application No. 18769813.9. (9 Pages).
Communication Pursuant to Article 94(3) EPC Dated Nov. 30, 2021 From the European Patent Office Re. Application No. 17780530.6. (4 Pages).
Communication Pursuant to Article 94(3) EPC Dated Jan. 31, 2020 From the European Patent Office Re. Application No. 17780530.6. (3 Pages).
Communication Pursuant to Article 94(3) EPC Dated Jan. 18, 2023 from the European Patent Office Re. Application No. 19211372.8 (7 Pages).
Communication Pursuant to Rules 70(2) and 70a(2) EPC Dated Sep. 7, 2018 From the European Patent Office Re. Application No. 16789407.0. (1 Page).
Communication Relating to the Results of the Partial International Search and the Provisional Opinion Dated Jun. 14, 2017 From the International Searching Authority Re. Application No. PCT/IL2017/050072. (12 Pages).
Communication Relating to the Results of the Partial International Search Dated May 8, 2014 From the International Searching Authority Re. Application No. PCT/IL2013/051059. (7 Pages).
Decision of Rejection Dated Jan. 14, 2020 From the Japan Patent Office Re. Application No. 2017-228103 and Its Translation Into English. (7 Pages).
European Search Report and the European Search Opinion Dated Jan. 3, 2022 From the European Patent Office Re. Application No. 21200149.9. (10 Pages).
European Search Report and the European Search Opinion Dated Feb. 4, 2020 From the European Patent Office Re. Application 19211372.8. (10 Pages).
Final Official Action Dated Mar. 6, 2023 from the US Patent and Trademark Office Re. U.S. Appl. No. 16/628,656. (22 pages).
Final Official Action Dated Nov. 9, 2021 from US Patent and Trademark Office Re. U.S. Appl. No. 15/274,756. (15 pages).
Final Official Action Dated Jun. 15, 2022 from US Patent and Trademark Office Re. U.S. Appl. No. 16/634,152. (19 pages).
Final Official Action Dated Dec. 28, 2020 from the US Patent and Trademark Office Re. U.S. Appl. No. 16/634,152. (29 pages).
Fluegge et al. "Precision of Intraoral Digital Dental Impressions With iTero and Extraoral Digitization With the iTero and A Model Scanner", American Journal of Orthodontics and Dentofacial Orthopedics, 144(3): 471-478, Sep. 2013.
Geng "Structured-Light 3D Surface Imaging: A Tutorial", Advances in Optics and Photonics, 3: 128-160, 2011.
Goshtasby et al. "A System for Digital Reconstruction of Gypsum Dental Casts", IEEE Transactions On Medical Imaging, 16(5); Oct. 1997, 11 pages.
International Preliminary Report on Patentability Dated Aug. 2, 2018 From the International Bureau of WIPO Re. Application No. PCT/IL2017/050072. (10 Pages).
International Preliminary Report on Patentability Dated Feb. 6, 2020 From the International Bureau of WIPO Re. Application No. PCT/IL2018/050825. (10 Pages).
International Preliminary Report on Patentability Dated Jul. 9, 2015 From the International Bureau of WIPO Re. Application No. PCT/IL2013/051059. (17 Pages).
International Preliminary Report on Patentability Dated Jan. 16, 2020 From the International Bureau of WIPO Re. Application No. PCT/IL2018/050731. (9 Pages).
International Preliminary Report on Patentability Dated Mar. 19, 2020 From the International Bureau of WIPO Re. Application No. PCT/IL2017/051014. (10 Pages).
International Preliminary Report on Patentability Dated Jul. 20, 2017 From the International Bureau of WIPO Re. Application No. PCT/IL2016/050023. (10 Pages).
International Preliminary Report on Patentability Dated Mar. 21, 2019 From the International Bureau of WIPO Re. Application No. PCT/IL2017/051015. (13 Pages).
International Preliminary Report on Patentability Dated Jul. 22, 2021 From the International Bureau of WIPO Re. Application No. PCT/IL2020/050040. (10 Pages).
International Preliminary Report on Patentability Dated Jul. 27, 2017 From the International Bureau of WIPO Re. Application No. PCT/IL2016/050058. (7 Pages).
International Preliminary Report on Patentability Dated Nov. 16, 2017 From the International Bureau of WIPO Re. Application No. PCT/IL2016/050449. (11 Pages).
International Search Report and the Written Opinion Dated Oct. 1, 2018 From the International Searching Authority Re. Application No. PCT/IL2018/050731. (16 Pages).
International Search Report and the Written Opinion Dated Sep. 2, 2014 From the International Searching Authority Re. Application No. PCT/IL2013/051059. (22 Pages).
International Search Report and the Written Opinion Dated Nov. 7, 2018 From the International Searching Authority Re. Application No. PCT/IL2018/050825. (17 Pages).
International Search Report and the Written Opinion Dated Aug. 8, 2017 From the International Searching Authority Re. Application No. PCT/IL2017/050072. (17 Pages).
International Search Report and the Written Opinion Dated Dec. 11, 2018 From the International Searching Authority Re. Application No. PCT/IL2017/051014. (18 Pages).
International Search Report and the Written Opinion Dated Apr. 18, 2016 From the International Searching Authority Re. Application No. PCT/IL2016/050058. (12 Pages).
International Search Report and the Written Opinion Dated Apr. 21, 2016 From the International Searching Authority Re. Application No. PCT/IL2016/050023. (14 Pages).
International Search Report and the Written Opinion Dated Aug. 23, 2016 From the International Searching Authority Re. Application No. PCT/IL2016/050449. (19 Pages).
International Search Report and the Written Opinion Dated Jul. 23, 2020 From the International Searching Authority Re. Application No. PCT/IL2020/050040. (14 Pages).
International Search Report and the Written Opinion Dated Jan. 24, 2018 From the International Searching Authority Re. Application No. PCT/IL2017/051015. (23 Pages).
Invitation to Pay Additional Fees, Communication Relating to the Results of the Partial International Search and the Provisional Opinion Dated Nov. 17, 2017 From the International Searching Authority Re. Application No. PCT/IL2017/051015. (17 Pages).
Invitation to Pay Additional Fees Dated May 12, 2020 From the International Searching Authority Re. Application No. PCT/IL2020/050040. (3 Pages).
Kolte A.P. et al., "Dimensional Influence of Interproximal Areas on Existence of Interdental Papillae," Journal of Periodontology, 2014, vol. 85, pp. 795-801, https://doi.org/10.1902/jop.2013.130361.
Logozzo et al. "Recent Advances in Dental Optics—Part I: 3D Intraoral Scanners for Restorative Dentistry", Optics and Lasers in Engineering, 54: 203-221, Mar. 2014.
Maintz et al. "A Survey of Medical Image Registration", Medical Image Analysis, 2(1): 1-37, Mar. 1998.
Medeiros et al. "Coded Structured Light for 3D-Photography: An Overview", IEEE-Rita, (Latin-American Learning Technologies Journal), IV(2): 109-124, Jul. 1999.
Non-Final Office Action for U.S. Appl. No. 17/211,640 dated May 10, 2023, 09 pages.
Notice Of Allowance Dated Aug. 9, 2018 From the US Patent and Trademark Office Re. U.S. Appl. No. 15/571,231. (17 pages).

(56) References Cited

OTHER PUBLICATIONS

Notice Of Allowance Dated Jul. 11, 2018 From the US Patent and Trademark Office Re. U.S. Appl. No. 15/115,196. (8 pages).
Notice Of Allowance Dated May 12, 2016 From the US Patent and Trademark Office Re. U.S. Appl. No. 14/655,286. (16 Pages).
Notice of Allowance Dated Jul. 13, 2021 from the US Patent and Trademark Office Re. U.S. Appl. No. 16/227,995. (7 pages).
Notice of Allowance Dated Nov. 30, 2020 from the US Patent and Trademark Office Re. U.S. Appl. No. 16/071,058. (10 pages).
Notice of Allowance Dated Nov. 9, 2022 from the US Patent and Trademark Office Re. U.S. Appl. No. 15/274,756. (8 pages).
Notice of Allowance for U.S. Appl. No. 16/628,656 dated Jul. 6, 2023, 8 pages.
Notice of Allowance for U.S. Appl. No. 16/634,152 dated Feb. 13, 2023, 11 pages.
Notice of Allowance for U.S. Appl. No. 17/211,640 dated Dec. 11, 2023, 10 pages.
Notice of Reasons for Rejection Dated May 7, 2019 From the Japan Patent Office Re. Application No. 2017-228103 and Its Translation Into English. (8 Pages).
Notice of Reasons for Rejection Dated Jul. 11, 2017 From the Japan Patent Office Re. Application No. 2015-548888 and Its Translation Into English. (5 Pages).
Notice of Reasons for Rejection Dated Feb. 14, 2017 From the Japan Patent Office Re. Application No. 2015-548888 and Its Translation Into English. (10 Pages).
Notice of Reasons for Rejection Dated Sep. 25, 2018 From the Japan Patent Office Re. Application No. 2017-228103 and Its Translation Into English. (15 Pages).
Notice Requesting Submission of Opinion Dated Feb. 3, 2021 From the Korean Intellectual Property Office Re. Application No. 10-2020-7032325 and Its Translation Into English. (14 Pages).
Notice Requesting Submission of Opinion Dated Apr. 26, 2019 From the Korean Intellectual Property Office Re. Application No. 10-2015-7020305. (4 Pages).
Office Action Dated Aug. 6, 2019 From the Israel Patent Office Re. Application No. 264237 and Its Translation Into English. (6 Pages).
Official Action Dated Sep. 3, 2021 from the US Patent and Trademark Office Re. U.S. Appl. No. 16/634,152. (43 pages).
Official Action Dated Nov. 4, 2020 From the US Patent and Trademark Office Re. U.S. Appl. No. 15/274,756. (19 Pages).
Official Action Dated Mar. 9, 2017 From the US Patent and Trademark Office Re. U.S. Appl. No. 15/115,196. (26 pages).
Official Action Dated Aug. 11, 2022 from US Patent and Trademark Office Re. U.S. Appl. No. 16/628,656. (10 pages).
Official Action Dated Jul. 11, 2024 from the US Patent and Trademark Office Re. U.S. Appl. No. 18/198,214. (46 pages).
Official Action Dated Jun. 12, 2020 from the US Patent and Trademark Office Re. U.S. Appl. No. 16/634,152. (41 pages).
Official Action Dated Dec. 13, 2017 From the US Patent and Trademark Office Re. U.S. Appl. No. 15/115,196. (26 pages).
Official Action Dated Jun. 13, 2019 From the US Patent and Trademark Office Re. U.S. Appl. No. 15/274,756. (39 pages).
Official Action Dated Feb. 15, 2024 from the US Patent and Trademark Office Re. U.S. Appl. No. 17/527,046. (41 pages).
Official Action Dated May 15, 2020 from the US Patent and Trademark Office Re. U.S. Appl. No. 16/071,058. (31 pages).
Official Action Dated Jul. 17, 2024 from the US Patent and Trademark Office Re. U.S Appl. No. 17/422,115. (28 pages).
Official Action Dated Jun. 17, 2021 from the US Patent and Trademark Office Re. U.S. Appl. No. 15/274,756. (16 pages).
Official Action Dated Dec. 19, 2023 from the US Patent and Trademark Office Re. U.S. Appl. No. 17/422,115. (61 pages).
Official Action Dated Feb. 19, 2021 From the US Patent and Trademark Office Re. U.S. Appl. No. 16/227,995. (27 Pages).
Official Action Dated Jul. 20, 2022 from US Patent and Trademark Office Re. U.S. Appl. No. 15/274,756. (25 pages).
Official Action Dated Oct. 26, 2022 from the US Patent and Trademark Office Re. U.S. Appl. No. 16/634,152. (15 pages).
Official Action Dated Sep. 28, 2016 From the US Patent and Trademark Office Re. U.S. Appl. No. 15/115,196. (19 pages).
Official Action Dated Apr. 3, 2020 from the US Patent and Trademark Office Re. U.S. Appl. No. 16/199,954. (31 pages).
OmniVision "OVM6946 400×400. Compact, Cost-Effective Wafer-Level Camera Module for Single-Use Endoscopes", OmniVision, Product Brief, 2 pages, Aug. 10, 2016.
Paperno et al. "A New Method for Magnetic Position and Orientation Tracking", IEEE Transactions on Magnetics, 37(4): 1938-1940, Jul. 2001.
Requisition by the Examiner Dated May 2, 2023 From the Innovation, Science and Economic Development Canada, Canadian Intellectual Property Office Re. Application No. 3,153,949. (4 Pages).
Requisition by the Examiner Dated Oct. 4, 2019 From the Innovation, Science and Economic Development Canada, Canadian Intellectual Property Office Re. Application No. 2,896,210. (3 Pages).
Requisition by the Examiner Dated Apr. 2, 07021From the Innovation, Science and Economic Development Canada, Canadian Intellectual Property Office Re. Application No. 2,896,210. (16 Pages).
Restriction Official Action Dated Nov. 14, 2019 From the US Patent and Trademark Office Re. U.S. Appl. No. 16/199,954. (6 pages).
Restriction Official Action Dated May 25, 2022 From the US Patent and Trademark Office Re. U.S. Appl. No. 16/628,656. (7 Pages).
Restriction Official Action Dated Sep. 26, 2018 From the US Patent and Trademark Office Re. U.S. Appl. No. 15/274,756. (10 Pages).
Restriction Official Action Dated Dec. 27, 2022 from the US Patent and Trademark Office Re. U.S. Appl. No. 17/211,640. (4 pages).
Salvi et al. "Pattern Codification Strategies in Structured Light Systems", Pattern Recognition, 37(4): 827-849, 2004.
Savarese et al. "3D Reconstruction by Shadow Carving: Theory and Practical Evaluation", International Journal of Computer Vision, 71(3): 305-336, Published Online Jun. 1, 2006.
Summons to Attend Oral Proceedings Pursuant to Rule 115(1) EPC Dated Jun. 5, 2024 From the European Patent Office Re. Application No. 19211372.8. (10 Pages).
Summons to Attend Oral Proceedings Pursuant to Rule 115(1) EPC Dated Mar. 18, 2022 From the European Patent Office Re. Application No. 18769813.9. (9 Pages).
Summons to Attend Oral Proceedings Pursuant to Rule 115(1) EPC Dated Mar. 19, 2020 From the European Patent Office Re. Application No. 13830124.7. (13 Pages).
Summons to Attend Oral Proceedings Pursuant to Rule 115(1) EPC Dated Mar. 19, 2021 From the European Patent Office Re. Application No. 17780530.6. (7 Pages).
Summons to Attend Oral Proceedings Pursuant to Rule 115(1) EPC Dated Apr. 20, 2021 From the European Patent Office Re. Application No. 17780530.6. (2 Pages).
Supplementary European Search Report and the European Search Opinion Dated Feb. 19, 2021 From the European Patent Office Re. Application No. 18837606.5. (7 Pages).
Supplementary European Search Report and the European Search Opinion Dated Aug. 21, 2018 From the European Patent Office Re. Application No. 16789407.0. (6 Pages).
Supplementary European Search Report and the European Search Opinion Dated Aug. 24, 2022 From the European Patent Office Re. Application No. 20739036.0. (9 Pages).
Supplementary European Search Report and the European Search Opinion Dated Feb. 2, 2023 from the European Patent Office Re. Application No. 22207979.0 (7 Pages).
Toshiba "IK-CT2: 0.7 × 0.7 mm, 220×220, CMOS", Toshiba Information Systems, Product Sheet, 1 page, Dec. 2016.
Translation of Ground(s) of Reason of Rejection Dated Nov. 19, 2021 From the Korean Intellectual Property Office Re. Application No. 2020-7032325. (4 Pages).
Translation of Notice Requesting Submission of Opinion Dated Jan. 21, 2020 From the Korean Intellectual Property Office Re. Application No. 10-2019-7034814. (6 Pages).
Translation of Notification of Apr. 15, 2016 From the State Intellectual Property Office of the People's Republic of China Re. Application No. 201380071840.0. (5 Pages).

(56) References Cited

OTHER PUBLICATIONS

Translation of Notification of Office Action Dated Jan. 5, 2017 From the State Intellectual Property Office of the People's Republic of China Re. Application No. 201380071840.0. (18 Pages).

* cited by examiner

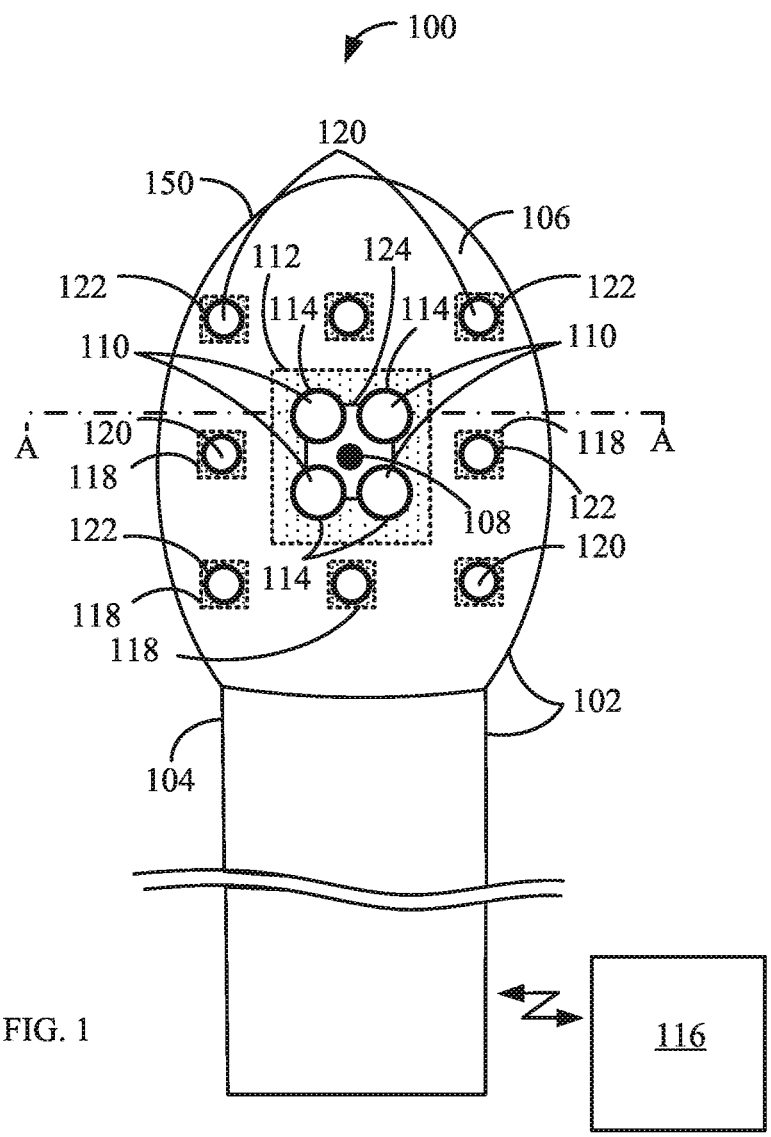
FIG. 1
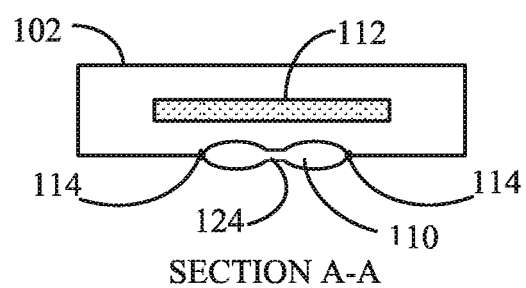
SECTION A-A

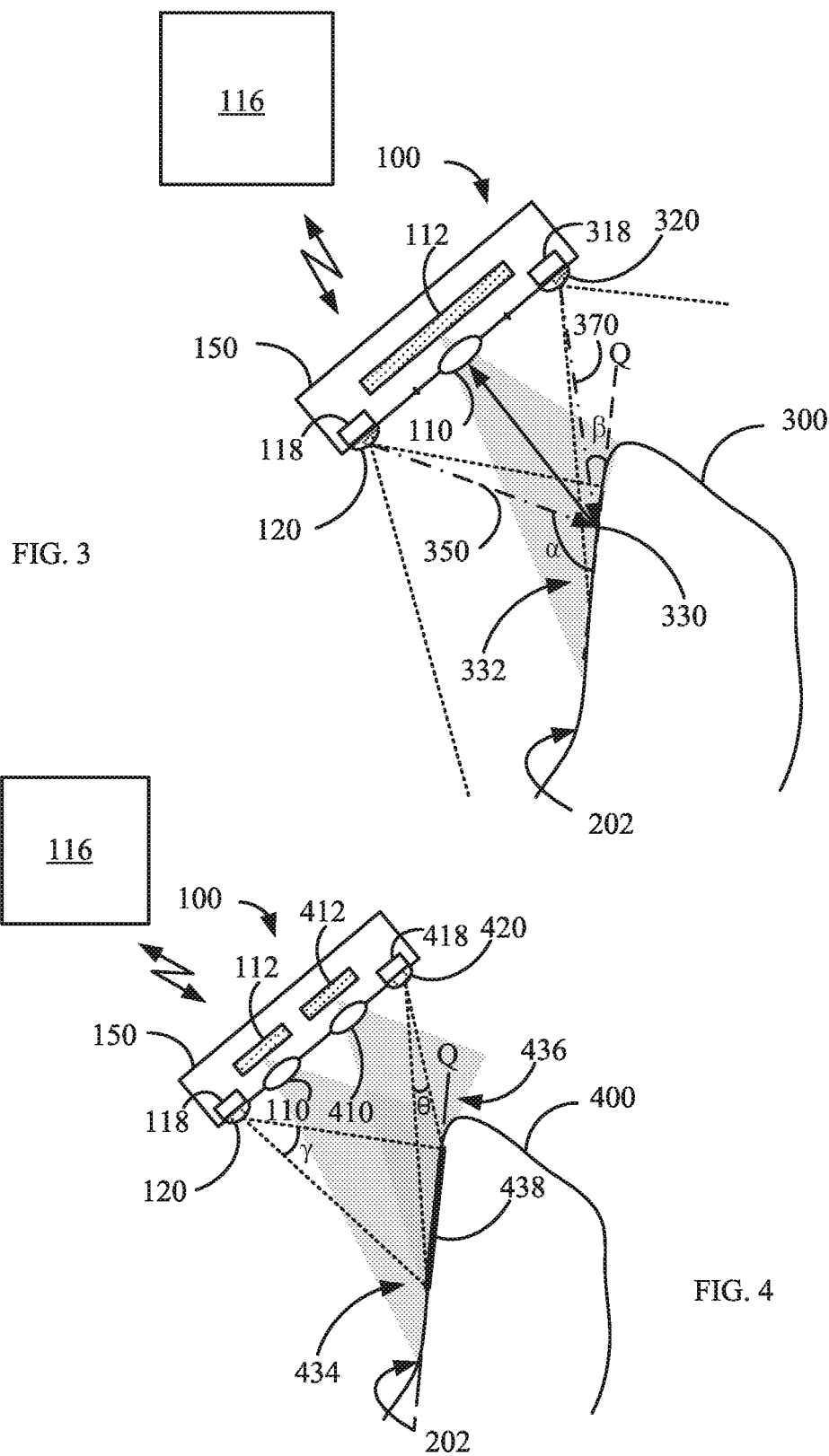

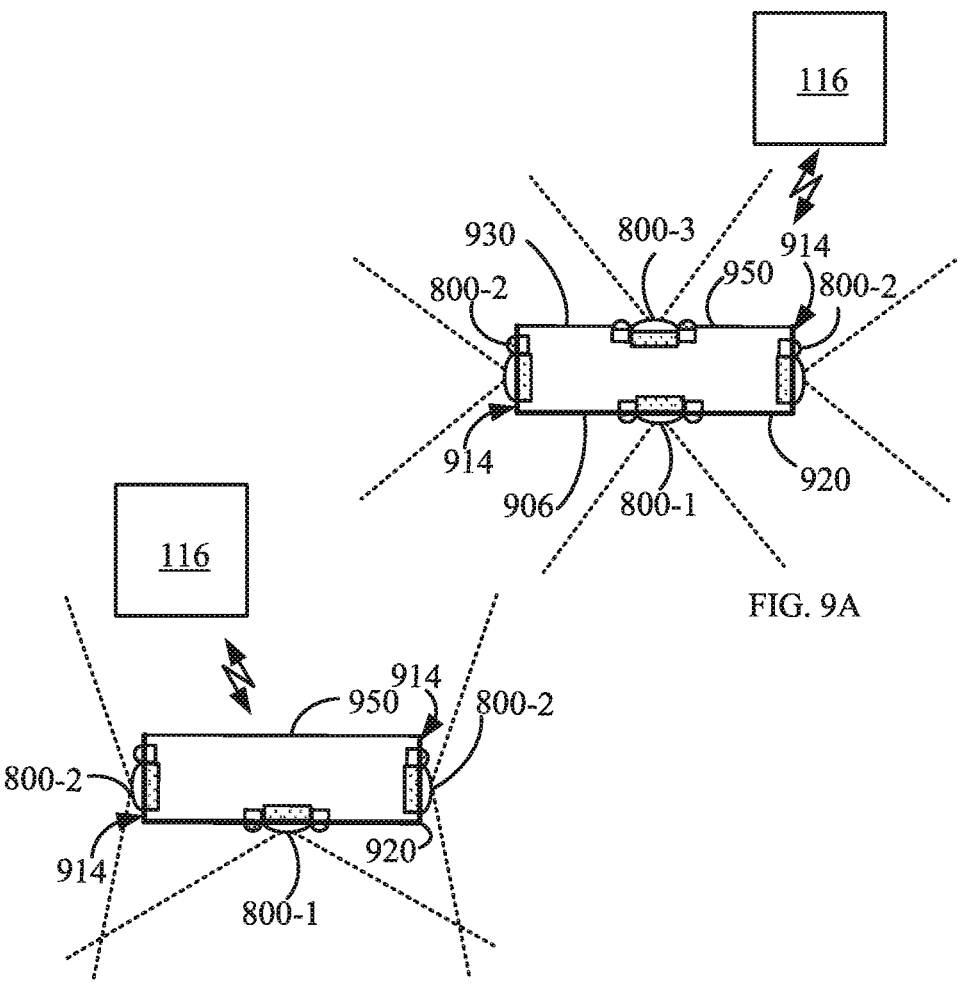
FIG. 9A
FIG. 9B
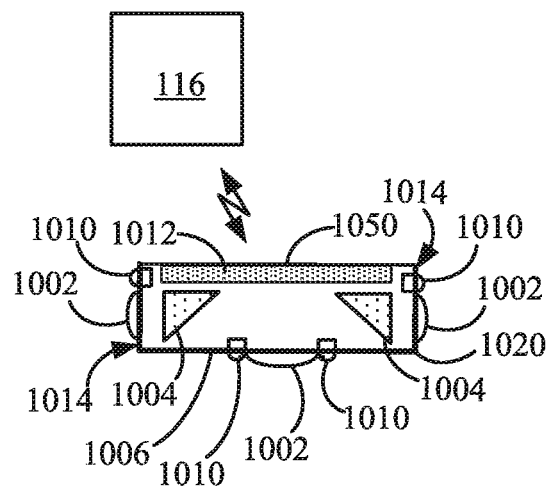
FIG. 10

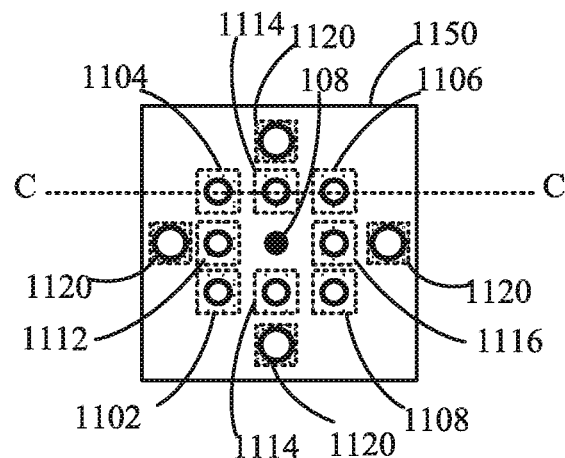
FIG. 11
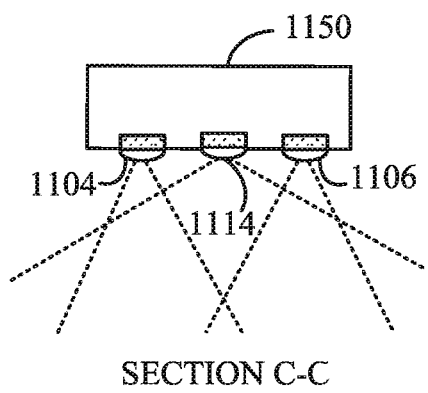
SECTION C-C
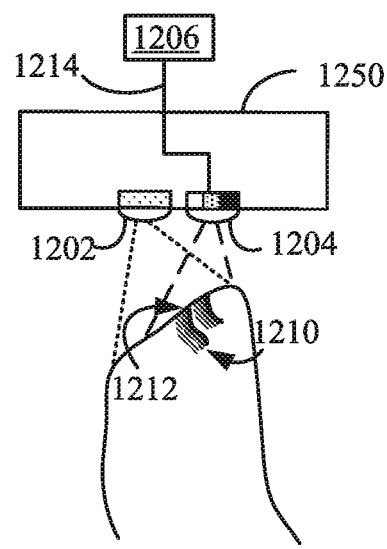
FIG. 12

INTRAORAL SCANNER

RELATED APPLICATIONS

This application is a continuation of U.S. patent application Ser. No. 17/211,640 filed on Mar. 24, 2021, entitled "Intraoral Scanner", which is a continuation of U.S. patent application Ser. No. 16/071,058 filed on Jul. 18, 2018 (U.S. Pat. No. 10,966,614), which is a U.S. 371 national stage application of, and herby claims priority to, PCT application no. PCT/IL2017/050072, entitled "Intraoral Scanner", filed Jan. 18, 2017, which claims benefit of and priority to U.S. provisional patent application No. 62/364,681, entitled "Intraoral Scanner," filed Jul. 20, 2016. PCT application no. PCT/IL2017/050072 is a continuation-in-part of PCT patent application no. PCT/IL2016/050058, entitled "System, Device, and Method for Dental Intraoral Scanning," filed on Jan. 18, 2016, which claims benefit of and priority to U.S. provisional patent application No. 62/104,835, entitled "System, Device, and Method for Dental Intraoral Scanning," filed on Jan. 18, 2015. Each of the preceding disclosures, in its entirety, is incorporated herein by reference.

FIELD AND BACKGROUND OF THE INVENTION

The present invention, in some embodiments thereof, relates to intraoral scanning systems and, more particularly, but not exclusively, to an intraoral scanner for acquiring a 3D image of a tooth.

The use of intraoral scanners (IOS) to size and acquire a 3D image of a tooth or teeth requiring restoration (e.g., for prostheses or model preparation) has become prevalent in dentist practices. However, commonly used IOSs combine the use of image sensors, light emitters, several lenses, mirrors, reflectors, beam splitters and other components the size and quantity of which contribute to a relatively large form factor and bulkiness of the IOS.

SUMMARY OF THE INVENTION

According to an aspect of some embodiments of the invention, there is provided a method for intraoral scanning, including: introducing an intraoral scanner (IOS) head into an oral cavity; acquiring an image of a region of interest (ROI); processing the acquired ROI image; and adjusting at least one image acquisition parameter other than exposure based on the processing.

According to some embodiments of the invention, the acquisition parameter includes a spatial orientation of the IOS head in respect to a region of interest (ROI).

According to some embodiments of the invention, the IOS includes at least a first light projector producing a first light beam and wherein the processing includes also estimation of a angle of incidence the first light beam on a surface of the ROI and where the adjusting is based on the estimated angle of incidence.

According to some embodiments of the invention, the acquisition parameter includes a direction and/or a rate of IOS head movement.

According to some embodiments of the invention, the processing includes analyzing at least one image property of the acquired image and determining adjustment of the at least one image acquisition parameter based on the at least one image and, wherein the adjustment includes at least one of: selecting and/or activating at least one imager, selecting and/or activating at least one light projector, deselecting and/or deactivating at least one imager, and deselecting and/or deactivating at least one light projector or combination thereof.

According to some embodiments of the invention, the adjustment includes signaling user to change spatial orientation of the IOS head.

According to some embodiments of the invention, the IOS head includes at least one imager and at least one light projector, and the acquisition parameter includes at least one of: at least one projected light parameter, a focal length of at least one IOS imager, a size of a field of view FOV of a sensor on the ROI, and a distance between at least one of one point of interest POI in the ROI and the imager, the POI and a light projector, and the imager and the light projector.

According to some embodiments of the invention, the IOS includes a first light projector and a second light projector and the adjustment.

According to some embodiments of the invention, the processing includes also estimation of an angle of incidence of a first beam of the first light projector over the ROI and estimation of an angle of incidence of a second beam of the second light projector over the ROI.

According to some embodiments of the invention, the estimated angle of incidence of the first beam is greater than the estimated angle of incidence of the second beam.

According to some embodiments of the invention, the processing includes tooth segmentation and locating the ROI on the segmented tooth and the adjustment is based on the segmentation.

According to some embodiments of the invention, the IOS includes an elongated element coupled to a first surface of the IOS, the first surface facing a region of interest (ROI), the method further including: contacting a location on the ROI with a portion of the elongated element, and wherein the adjustment includes selecting at least one image acquisition parameter producing an image from which a position of the location can be determined more accurately that a previous parameter.

According to some embodiments of the invention, the adjustment includes activating a light emitter to illuminate a third surface of the elongated element, the third surface generally opposite the portion of the elongate element that contacts the ROI.

According to some embodiments of the invention, the location is under a gum line.

According to some embodiments of the invention, adjustment also includes selecting an imager oriented with the third surface generally facing the selected imager and located between the selected imager and the ROI.

According to some embodiments of the invention, the method further includes casting a structured light pattern on the ROI, and adjusting the pattern based on the processing.

According to some embodiments of the invention, the processing includes also estimation of a contrast of the structure light over the ROI and wherein the adjusting is controlled by the processor to improve the contrast.

According to some embodiments of the invention, the processor estimates a movement of the IOS and wherein the adjusting is based on at least one of the movement and a predicted future spatial relationship between the IOS head and a region of interest.

According to some embodiments of the invention, the adjusting is based on a current or estimated future spatial relationship between the IOS and the ROI.

According to some embodiments of the invention, the spatial relationship includes at least one of a location and an orientation.

According to some embodiments of the invention, the method further includes projecting a patterned light onto the ROI and correlating a pattern of the patterned light with the spatial relationship.

According to an aspect of some embodiments of the invention, there is provided an intraoral scanner (IOS) including: an IOS head including at least one imager imaging a field of view (FOV); at least one light projector configured for illuminating the FOV; and circuitry configured for at least one of processing an image acquired by the imager and adjusting at least one image acquisition parameter other than exposure based on the processing.

According to some embodiments of the invention, the IOS includes multiple optical components having multiple apertures and wherein the multiple optical components include the at least one imager and the one light projector.

According to some embodiments of the invention, the adjusting is achieved without moving parts.

According to some embodiments of the invention, the IOS head has a width of less than 3 cm and is mounted on a distal portion of a handle of length between 10 to 40 cm.

According to some embodiments of the invention, the IOS head has a longitudinal axis at an angle of between 85 to 60 degrees of a proximal portion of the handle.

According to some embodiments of the invention, the IOS head includes a probe at having a distal portion thereof at an angle of between 85 to 60 degrees to a proximal portion of the handle.

According to some embodiments of the invention, the IOS head includes a probe and a plurality of imagers and a plurality of light projectors located around the probe.

According to some embodiments of the invention, the acquisition parameter includes at least one of: spatial orientation of the IOS head in respect to a region of interest (ROI), direction and rate of IOS head movement, focal length of IOS imager, a size of the FOV, a distance between at least one of the ROI and the imager, the ROI and a light projector, and the imager and the light projector.

According to some embodiments of the invention, the at least one light parameter includes at least one of: a number of light projectors, a light intensity, a projected structured light pattern, light coherence, wavelength, duration of light, pulsed light, continuous light, pulse frequency and structured light pattern, a power level of the projector, a flicker time of the projector.

According to some embodiments of the invention, the IOS head includes at least one optical transmitter/receiver wafer level optics (WLO) module which includes the imager and light projector.

According to an aspect of some embodiments of the invention, there is provided an intraoral scanner (IOS) including: one or more imagers and one or more light projectors, some imagers and projectors formed on one or more interconnected boards at least one of the imagers having a first optical aperture and having different external dimensions from at least one of the light projectors, the at least one light projector having a second optical aperture; and wherein the first optical aperture and the second optical aperture are located on a plane perpendicular to a mean line of sight of the at least one imager and the at least one light projector.

According to some embodiments of the invention, the one or more interconnected boards includes at least one of a staggered rigid PCB, a planar PCB, and a flexible PCB.

According to some embodiments of the invention, the IOS further includes a plurality of imaging apertures for imaging by one or more imagers, wherein at least two of the plurality of apertures is configured for imaging at different focal distances.

According to some embodiments of the invention, the plurality of imaging apertures are all located on the plane perpendicular to the mean line of sight.

According to an aspect of some embodiments of the invention, there is provided an intraoral scanner (IOS) including: a multi-layered WLO module including a top layer including at least one imager and at least one light projector; and a second layer including at least one structured light transparency device.

According to some embodiments of the invention, the IOS further includes a bottom layer including at least one microlens positioned along an optical path of at least of the light projector and the imager.

According to some embodiments of the invention, at least two of the layers are separated by a spacer frame.

According to some embodiments of the invention, the spacer frame includes an optical element including at least one of a condensing element and a diffusing element.

According to some embodiments of the invention, the bottom layer is configures as a glass molded array or polymer lenses on a glass wafer.

According to some embodiments of the invention, the bottom layer further includes at least one projection microlens including a pair of lenses disposed on both sides of the wafer.

According to some embodiments of the invention, the imager and the light projector face the bottom layer.

According to some embodiments of the invention, the top layer further includes a light projector spacer frame including PCB or Si wafer with at least one mounted light projector.

According to some embodiments of the invention, the layers also include a mid-layer glass wafer having a clear portion corresponding to an image receiving area of the imager.

According to some embodiments of the invention, the clear portion is coated with a filtering coat.

According to some embodiments of the invention, the IOS head includes: a first surface facing a first region of interest, a second surface and a third surface, each attached to the first surface on opposite sides thereof and facing a second region of interest and a third region of interest, respectively, and at least one optic transmitters/receivers wafer level optics (WLO) module disposed on each of the surfaces.

According to some embodiments of the invention, the IOS head includes a first surface facing a first region of interest, a second surface and a third surface, each attached to the first surface on opposite sides thereof and facing a second region of interest and a third regions of interest, respectively, and at least one imaging lens disposed on each of the surfaces.

According to some embodiments of the invention, an image received by at least one lens disposed on the second and/or third surfaces is imaged on at least a portion of the imager via a mirror or a prism.

According to some embodiments of the invention, the light projector is a coherent light generator that generates a diffractive light pattern on an ROI, the light pattern including at least two different wavelengths.

According to an aspect of some embodiments of the invention, there is provided a method for intraoral scanning, including: positioning an intraoral scanner (IOS) head inside an oral cavity; acquiring consecutive images of a region of interest (ROI); processing the acquired images; and predicting at least one future location and/or spatial orientation of the IOS head based on the processing.

According to some embodiments of the invention, the method further includes analyzing at least one image property of at least one of the acquired images and determining at least one future adjustment of at least one image acquisition parameter based on at least one of the image property and the prediction.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product.

Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such acquiring an image employing an intraoral scanner, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a plan view and cross-section view thereof at level A-A simplified illustration of a surface of an intraoral scanner (IOS) facing a region of interest (ROI) in accordance with embodiments of the current invention;

FIG. 3 is a cross-section view simplified illustration of an example of implementation of scanner optics in accordance with embodiments of the current invention;

FIG. 4 is a cross-section view simplified illustration of an example of implementation of scanner optics;

FIGS. 9A and 9B are cross section view simplified illustrations of embodiments of an IOS head in accordance with embodiments of the current invention;

FIG. 10 is a cross section view simplified illustration of an embodiment of an IOS head in accordance with embodiments of the current invention;

FIG. 11 is a plan view and cross section view thereof at level C-C simplified illustration of an embodiment of an IOS head in accordance with embodiments of the current invention;

FIG. 12 is a cross-section view simplified illustration of an embodiment of an IOS head in accordance with embodiments of the current invention;

DESCRIPTION OF SPECIFIC EMBODIMENTS OF THE INVENTION

Figure 2A:
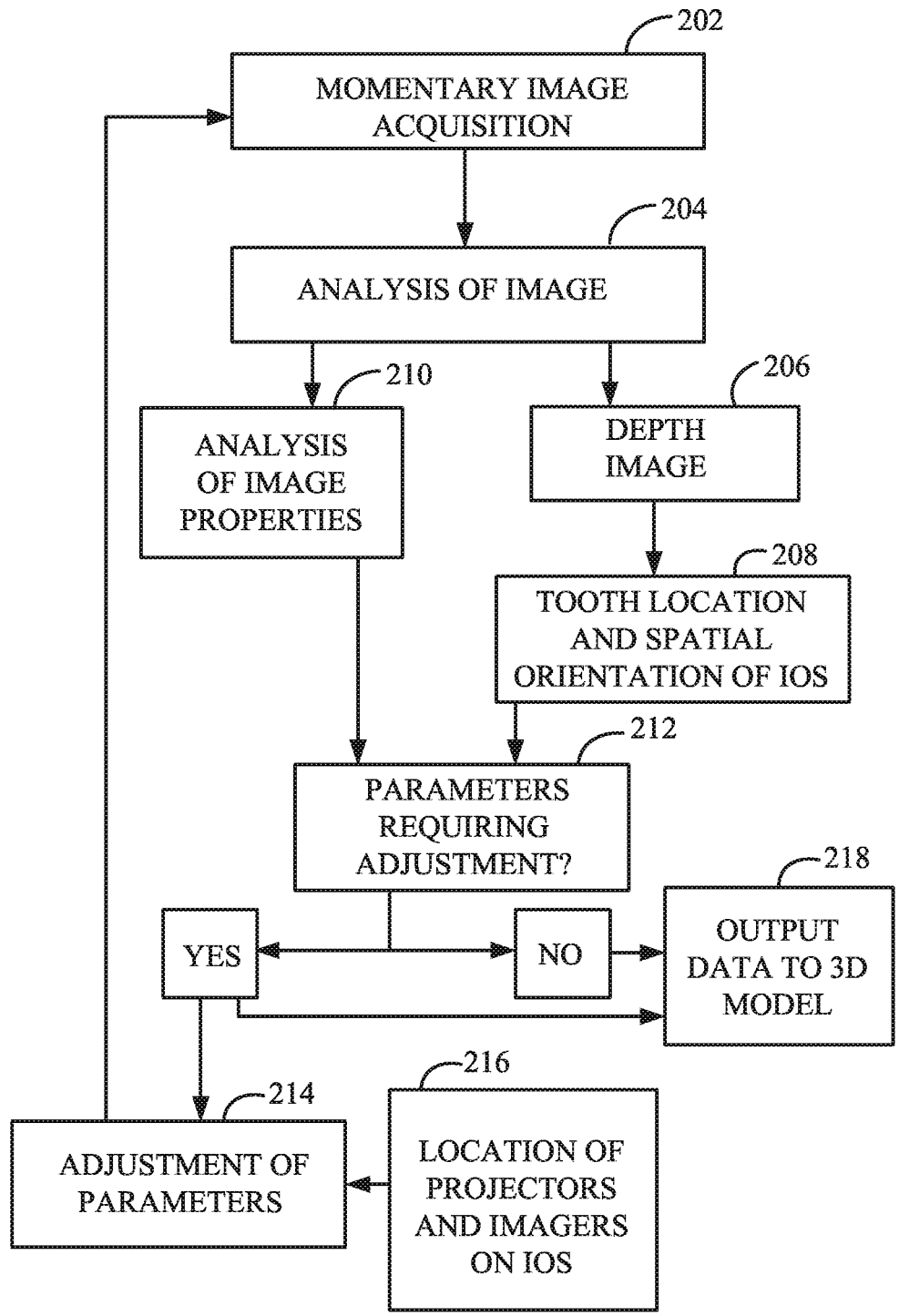
FIGS. 2A and 2B are flow charts of a processing operation of an image acquired by an IOS head in accordance with embodiments of the current invention.

The present invention, in some embodiments thereof, relates to intraoral scanning systems and, more particularly, but not exclusively, to an intraoral scanner for acquiring a 3D image of a tooth.

Intraoral scanners (IOS) typically combine the use of several optical components, e.g., image sensors, light emitters, lenses, mirrors, reflectors, beam splitters and other components the size of which oftentimes contributes to a relatively large form factor and bulkiness of the IOS.

An aspect of some embodiments of the invention relates to a downscaled multi aperture optics intraoral scanner (IOS) head having a small form factor. In some embodiments of the invention, the IOS is in the form and size of a common dental turbine. In some embodiments, the IOS includes a head having an image sensor that defines an optical field of view and communicates a received image to a processing unit that processes received images into a 3D image. In some embodiments, the IOS includes an elongate element fixedly or movably coupled to a surface of the IOS facing a region of interest (ROI). In some embodiments, the elongated element may be angled in reference to the surface of the IOS facing a region of interest (ROI). In some embodiments, the elongated may be generally normal to the surface of the IOS facing a region of interest (ROI). In some embodiments, the IOS head width may be between 5-25 mm. In some embodiments, the IOS head width may be between 3-20 mm. In some embodiments, the IOS head width may be between 1-15 mm. In some embodiments, the IOS head length may be between 3-20 cm. In some embodiments, the IOS head width may be between 5-25 mm. In some embodiments, the IOS head thickness may be between 10-20 mm. In some embodiments, the IOS head thickness may be between 5-15 mm. In some embodiments, the IOS head thickness may be between 3-10 mm.

In some embodiments, an IOS may have few or no moving parts. For example, the viewing adjustments may be without moving parts. For example, the optical portion of the IOS may contain no moving parts. For example, the IOS may have multiple optical apertures and/or changing a direction of illumination and/or a direction of viewing and/or a focal length and/or a field of view may be achieved by activating various devices associated with various optical apertures but without moving those devices with respect to the IOS and/or each other. Using multiple apertures optionally facilitates adjusting of optical parameters such as focal length and/or field of view with fewer and/or without moving parts. In some embodiments, a device fewer and/or without moving parts may be smaller and/or more reliable than a device having more moving parts. In some embodiments, a device having fewer and/or no moving parts may be more easily controlled by a process, for example for automated control of optical parameters than a device with more moving parts. For example, control may be via simple transistors and/or switches without requiring, for example, positions sensors.

In some embodiments, the elongate element is disposed in the face of the IOS. In some embodiments, the elongate element is disposed off center of the face of the IOS. For example, the elongate element may be perpendicular to a surface facing a ROI. In some embodiments, the elongate element is shaped like a stylus. In some embodiments, the elongate element is telescopic and may vary in length. In some embodiments, the elongate element includes one or more of an image sensor, an imaging lens, a micro light emitter and a structured light transparency. In some embodiments, an elongated object may include a probe, for example a dental probe. Optionally the elongated object is straight. Alternatively or additionally, the elongated object may be bent, angled or curved. For example, the elongated object may be configured for probing locations under a gum line. Optionally a sensor is provided to sense when an elongated object is in contact with a ROI. Optionally, a processor is configured to compute and/or adjust viewing parameters to facilitate and/or increase accuracy of determination of a point of contact between the elongated object and the ROI based on an image and/or a set of images.

In some embodiments of the invention, the image sensor is disposed on a surface of the IOS facing a first region of interest (ROI). In some embodiments, the IOS includes more than one image sensor. In some embodiments, the image sensor includes an array of micro image sensors. In some embodiments, the image sensor is manufactured by wafer level optics technology (WLO). In some embodiments, the image sensor is between 0.1 mm and 150 mm. In some embodiments, the image sensor(s) cover(s) between 10 and 90 percent of the IOS head surface facing a first region of interest (ROI). In some embodiments, the image sensor/s cover(s) between 20 and 80 percent of the IOS head facing a first region of interest (ROI). In some embodiments, the image sensor(s) cover(s) between 30 and 70 percent of the IOS head facing a first region of interest (ROI).

In some embodiments of the invention, the scanner includes one or more imaging microlenses disposed between the image sensor and the ROI that project a received image onto the image sensor. In some embodiments, a single final microlens is disposed between the image sensor and the ROI. In some embodiments, several imaging microlenses project overlapping images on the image sensor. In some embodiments, several imaging microlenses project images on separate corresponding segments of the image sensor. In some embodiments, a single imaging microlens comprises several imaging microlens elements. In some embodiments, a single imaging microlens comprises an array of microlens elements. In some embodiments, the imaging microlens is manufactured by wafer level optics (WLO) technology. In some embodiments, each imaging microlens element projects an image on a portion of the image sensor. In some embodiments, the imaging microlenses are disposed inside apertures in the surface of the IOS. In some embodiments, the image sensor is disposed inside the IOS head, deep to the apertures of the imaging microlenses.

In some embodiments, imaging microlens array is bonded to a single image sensor. In some embodiments, the microlens array is bonded to an array of image sensors. In some embodiments, the imaging microlens array is a glass molded array. In some embodiments, the imaging microlens array is made of polymer microlenses on a glass array. In some embodiments, the image sensor is produced on a silicon wafer. In some embodiments, an array of image sensors on a wafer is bonded to an L array of microlenses and diced together with the attached image lens array to produce individual bonded image sensor-micro lens modules. In some embodiments, the imaging lens is made of metamaterials.

In some embodiments, the IOS is mirrorless. In some embodiments all IOS components (i.e., image sensor, imaging lens, light emitter, projecting lens and structured light micro transparency) necessary to acquire a 3D image, for example, a computer 3D model are located in the head of the IOS. In some embodiments, every light ray incident on a single final imaging lens continues travel directly to the image sensor.

In some embodiments a processing unit digitally stitches (i.e., integrates or attaches) image segments received from the image sensor. In some embodiments, a processing unit optically stitches image segments received from the image sensor. In some embodiments, the processing unit processes image segments received from the image sensor without stitching. In some embodiments, the IOS includes circuitry that controls IOS components (e.g., micro light emitters, micro structured light emitters) based on received image information. In some embodiments, the IOS includes circuitry that controls IOS components (e.g., micro light emitters, micro structured light emitters) based on input from the processing unit. In some embodiments, acquired image segments of a single field of view (FOV) are projected on the image sensor. In some embodiments, each acquired segment includes a complete FOV. In some embodiments, the processing unit processes received image information in real time.

In some embodiments of the invention, the IOS includes one or more light emitters that project light in the general direction of the ROI. In some embodiments, the IOS includes a plurality of light emitters that project light in the general direction of the ROI. In some embodiments, a plurality of light emitters is generally distributed about the elongate element. In some embodiments, the IOS includes two light emitters each on either side of the elongate element. In some embodiments, a micro light emitter casts structured light on a tooth. In some embodiments, structured light is projected via projection microlenses. In some embodiments, the micro light emitter is independent of the IOS.

In some embodiments of the invention, the projection lenses are micro optic projection lens. In some embodiments, the projection microlenses are low modulation transfer function (MTF) microlenses. In some embodiments, the projection microlenses are disposed in an aperture. In some embodiments, the aperture is less than 2 mm in diameter. In some embodiments, the aperture is less than 1 mm in diameter. In some embodiments, the aperture is less than 0.5 mm in diameter. In some embodiments, the projection microlenses are refractive projection microlenses. In some embodiments, the projection microlenses are diffractive optic elements (DOE). In some embodiments, the projection microlenses are a combination of a refractive and diffractive microlenses.

In some embodiments of the invention, a projection microlens comprises a microlens wafer level optics array. In some embodiments, projection microlenses and imaging lenses are produced on the same lens array to provide mechanical stability and tight tolerances at low cost. In some embodiments, the projection microlens array is a glass molded array. In some embodiments, the projection microlens array is made of polymer microlenses on a glass array. In some embodiments, the projection lens is made of metamaterials.

An aspect of some embodiments of the invention relates to image pattern optimization. In some embodiments, the IOS communicates a received image of a tooth from the image sensor to a processing unit that, in turn, processes the acquired image for example for generating a 3D image (e.g., 3D computer model) of the tooth. In some embodiments processing the acquired image includes analysis of properties of an acquired image and automatically adjusting acquisition parameters based on the processing. In some embodiments, the processing unit processes a received image and automatically based on the processing, selects or signals IOS circuitry to selects one or more of the plurality of micro light emitters a ray of which is incident on an axial surface of an imaged tooth at an angle from the surface thereof. Optionally the processor may segment a tooth and/or estimate 3D orientation of segments of a surface of the tooth. Optionally the processor may estimate an angle of incidence of a beam on a ROI. For example the estimated angle may account for a location of a light emitter and/or the angle of a surface segment in the ROI. In some embodiments the processing unit analyzes a received image and, based on the processing, automatically selects and activates one or more of the plurality of micro light emitters. For example, the processing unit may select and/or activate an emitter producing a beam having largest portion incident on a ROI and/or an emitter producing a beam having a direction closer to perpendicular to the ROI. For example, the ROI may be an axial surface of an imaged tooth. Alternatively or additionally, the processing unit may turn off or dim one or more non-selected emitters.

An aspect of some embodiments of the invention relates to movement of the IOS head. When the IOS is moved, the processing unit continuously or in quick succession processes received images at each point in time and/or automatically adjusts acquisition parameters based on the processing. In some embodiments, based on the processing the processing unit or IOS circuitry selects and activates one or more of the plurality of micro light emitters a ray of which is incident on an axial surface of the tooth at an angle between 30 and 90 degrees from normal the axial surface of the tooth. In some embodiments when the IOS is moved the processing unit continuously or in quick succession analyzes received images at each point in time and/or based on the processing automatically selects and activates one or more of the plurality of micro light emitters a largest portion of a beam angle of which is incident on an axial surface of an imaged tooth along to the axial dimension thereof and/or turns off or dims non-selected micro light emitters.

In some embodiments of the invention when the processing indicates contact of the elongate element with an axial surface or any other surface of an imaged tooth, the processing unit automatically adjusts acquisition parameters based on the detected contact. In some embodiments of the invention when the processing indicates contact of the elongate element with an axial surface or any other surface of an imaged tooth, the processing unit or IOS circuitry activates a light emitter that illuminates a side of the element not in contact with or opposite to the side of the element in contact with the axial surface of the tooth.

In some embodiments of the invention the IOS includes several imaging sensors and micro light emitters distributed about the elongate element and when the elongate element is placed in contact with the axial wall or any other surface of a tooth at locations around the circumference of the tooth, the processing unit or IOS circuitry activates one or more a light emitters that illuminate a side of the element not in contact with or opposite to the side of the element in contact with the axial wall of the tooth.

An aspect of some embodiments of the invention relates to a downscaled IOS including one or more structured light casting micro-transparencies disposed between a micro light emitter and a projection microlens and cast structured light on a ROI. In some embodiments, the projection microlens casts structured light on the ROI. In some embodiments, the pattern is manually fitted to the direction of movement of the scanner and spatial orientation of the scanner in respect to the tooth being scanned. In some embodiments, the pattern is automatically fitted to the direction of movement spatial orientation of the scanner in respect to the tooth being scanned. In some embodiments, the structured light patterns and stereo or multiviews of oral features can be combined at the processing unit. In some embodiments, several micro light emitters project several overlapping structured light pattern orientations illuminate a common portion of the ROI in the field of view.

In some embodiments of the invention the processing unit processes a received projected structured light image and based on the processing automatically activates a micro light emitter that casts structured light providing the most precise image information. In some embodiments, the processing unit processes the received images including projected structured light and automatically selects and activates a micro light emitter that casts structured light having the highest contrast and/or resolution.

In some embodiments of the invention, the IOS includes a micro light emitter that projects light at two or more wavelengths. In some embodiments, the projecting microlens is a diffractive optical element (DOE) that creates a given pattern at two or more wavelengths such that the patterns differ by the wavelengths ratio. In some embodiments, the IOS includes an RGB light source. For example, the RGB light source may be behind the DOE and/or remote from the IOS head. For example, light may be transferred from a remote RGB light source with fiber optic delivery. In some embodiments, the IOS includes a multi wavelength light source including at least two wavelengths near the blue. In some embodiments, the RGB micro light emitter emits RGB light through a DOE. In some embodiments, the image sensor receives three separate pattern images at three different wavelengths cast on the field of view by the RGB micro light emitter. Optionally a processor may estimate a contrast of a projected pattern on a ROI. For example, the contrast estimate may account for incidence angle of the pattern on the ROI, distance from the ROI, power of a light emitter, and/or direction of features in the pattern.

An aspect of some embodiments of the current invention relates to an IOS having a form that is a familiar and/or convenient for a dentist. In some embodiments, the IOS may be shaped similar to and/or be configured as an add-on to a dental instrument. For example, the dental instrument may include a drill and/or a probe. Optionally, one or more projectors may cast light onto a ROI. For example, a processor may select and/or activate and/or deselect and/or deactivate a projector based on an incidence of the light and/or a projected pattern on the ROI and/or according to a movement of the IOS. Optionally, one or more sensors may image the ROI. For example, a processor may select and/or activate and/or deselect and/or deactivate a sensor based on a FOV on the ROI and/or according to a movement of the IOS. Optionally, the IOS may be configured to collect 3D data above and/or below a gingival border. For example, the IOS may include a probe and/or may be used in conjunction with a probe to gather 3D data under the gingival border.

In some embodiments, an IOS probe may include an angled handle. Optionally, a handle may have a proximal portion adapted to be held by a dentist and/or a distal portion adapted to be inserted into the mouth of a patient. For example, the angle between an axis of the distal portion and the axis of the proximal portion of the angled handle may range between 0 to 10 degrees and/or between 10 to 30 degrees and/or between 30 to 60 degrees. For example, the angle between an axis of the distal portion and the axis of the IOS head may range between 90 to 80 degrees and/or between 80 to 60 degrees and/or between 60 to 30 degrees.

In some embodiments, an IOS tool may include a probe. Optionally the length of the probe may range between 0 to 5 mm and/or between 5 to 15 mm and/or between 15 mm to 25 mm and/or between 20 to 40 mm. Optionally the probe may have an average width ranging between 0 to 0.1 mm and/or between 0.1 mm to 0.3 mm and/or between 0.3 to 1 mm and/or between 1 mm to 3 mm. Optionally the probe may include fiduciary markers and/or graduations for example indicating a distance of a point on the probe from the tip of the probe.

In some embodiments, an IOS may be used to explore regions under a gum line. For example, an IOS may include a probe. The probe may be used to explore regions below a gum line. Images produced by the IOS may be used to define the location of the probe and/or a feature touched by the probe under the gum line and/or to relate features imaged above the gum line to features explored below the gum line. The depth, angle and/or directional relationship between the probe tip under the gum line and/or revealed structures above the gum line are optionally estimated via image processing. Optionally, a light source and/or an imager may be selected and/or deselected in order to improve an estimation of a location of a probe tip under a gum.

An aspect of some embodiments of the current invention relates to an IOS having optical components mounted to have synchronized and/or complimentary focal lengths and/or fields of view. For example, an imaging sensor and/or a light emitter of different dimensions may be mounted to have optical apertures along a plane facing a ROI and/or at a fixed distance from a ROI. For example, the optical components may be mounted with their optical apertures distributed along a plane perpendicular to the average direction of the beams of the emitters and/or average viewing direction (e.g. the directions to which the sensors face e.g. the line of sight of the viewer) and/or the combined average direction. For example, the average direction may be the unweighted average of vectors, each vector being an average direction of a beam of an emitter and/or an average viewing direction of a sensor. For example, a long element may be set back in relation to a short element. For example, setting back the long element may cause the optical apertures of the two elements to fall on a plane perpendicular to the mean viewing/beam direction. Alternatively or additionally, components with different focal lengths may be mounted at different heights to form a common FOV. Alternatively or additionally, components of similar focal length may be mounted at different heights to create an array of components having a longer depth of field. For example, the components may be mounted on staggered PCB's and/or on a flexible PCB and/or with spacers.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General Configuration of IOS Head

The various optical components of the IOS (e.g., image sensor, imaging lens, projection lens, etc.) appear in the drawings in small scale numbers or as small groups of individual components, however the components depicted in the drawings are only representative of optical transmitters and receivers that consist of many independently located apertures, each component within an array controlled and activated individually or, alternatively, all operated as a unified coherent (or at least partially coherent) array. Each of the optical transmitters and receivers may include dozens and even hundreds of corresponding micro wafer level component arrays and/or individual modules. The optical IOS elements (e.g., imaging microlens, image sensor, projection lens, structured light micro transparency, etc.) in this disclosure relate, in some embodiments, but not exclusively, to micro lens arrays such as, for example, wafer level optics (WLO) components or individual lenses camera/projector modules.

Reference is now made to FIG. 1, which is a plan view and cross-section view thereof at level A-A (Section A-A) simplified illustration of a surface of a multiaperture optics intraoral scanner (IOS) head facing a region of interest (ROI), e.g., a tooth. As shown in FIG. 1, an IOS 100 includes a housing 102 shaped and sized to fit into an oral cavity with a head portion 150 and a handle portion 104. Handle 104 may be at various lengths indicated by two S-shaped break lines traversing the handle and sized to be optionally handled from outside the oral cavity. For example, a user may use a handle outside the oral cavity to manipulate the scanner inside the oral cavity. Optionally, handle 104 may house one or more components of IOS 100.

Optionally, IOS 100 may be in the form and size of a common dental turbine. Optionally, in some embodiments IOS head 150 width may be between 5-25 mm. In some embodiments IOS head 150 width may be between 3-20 mm. In some embodiments, IOS head 150 width may be between 1-15 mm, less than 1 mm or more than 15 mm. In some embodiments IOS head 150 length may be between 3-20 cm. In some embodiments IOS head 150 width may be between 5-25 mm. In some embodiments, IOS head 150 thickness may be between 10-20 mm, less than 10 mm or more than 20 mm. In some embodiments IOS head 150 thickness may be between 5-15 mm. In some embodiments, IOS head thickness may be between 3-10 mm, less than 3 mm or more than 10 mm.

As shown in FIG. 1, in some embodiments first surface 106 of intraoral scanner (IOS) 100 facing a region of interest (ROI) may include a plurality of imaging microlenses 110 or microlens arrays, disposed between one or more imagers or image sensors 112 and the ROI being scanned. As used herein the terms "Imager" and Image Sensor" are used interchangeably and apply generally to any image acquisition sensor.

Optionally, imaging microlenses 110 may be disposed within apertures 114 in first surface 106 and as will be explained in greater detail below project acquired images on one or more image sensor 110 or segments thereof. One or more image sensor 112 may be disposed within head 150 and deep to imaging microlenses 110.

In the embodiment of FIG. 1 and as will be explained in greater detail below, imaging microlens 110 may be an array 124 of microlenses, an array 124 of four microlenses is depicted in the example of FIG. 1. Each of array 124 microlenses optionally separately projects an image on a segment of image sensor 112. In some embodiments, acquired fields of view (FOVs) projected onto image sensor 112 by individual segments of imaging microlens array 124 at least partially overlap each other. The received image or images may be communicated by wire or wirelessly to a processing unit 116 for processing. In some embodiments a single final microlens 110 is disposed between image sensor 112 and the ROI so that a light ray incident on final microlens 110 continues travel directly to image sensor 112, i.e., a light ray traveling between final microlens 110 and image sensor 112 does not encounter any intermediate optical component on its way that changes the direction of travel (e.g., diverges, splits, bends, reflects or any other similar effect) of the light ray or at least a portion thereof.

IOS 100 head 150 may also include one or more micro light emitters 118 that emit light directly or through one or more projecting microlenses 120 in the general direction of an ROI. In some embodiments light emitter 118 may be at least one of a Surface-Mounted-Device Light-Emitting Diode (SMD LED) Module, a Chip on Board (COB) LED, a multi-COB (MCOB), an edge emitting Laser, a vertical-cavity surface-emitting laser (VCSEL) or a coherent or incoherent light delivery via optical fiber. In some embodiments, light emitters 118 may be controllably and mechanically moveable, e.g., mounted on a MEMS device.

In FIG. 1, a plurality of projecting microlenses 120, eight are depicted in FIG. 1, are disposed about or to one side of elongate element 108 located optionally centrally on surface 106. Optionally, projecting microlenses 120 may be disposed within apertures 122 in first surface 106 between one or more micro light emitters 118 and the ROI being illuminated. In some embodiments a single final projecting microlens is disposed between the light emitter and the ROI so that a light ray projected from one or more light emitters 118 travels directly to and is incident on projecting microlens 120, a light ray traveling between final microlens 110 and image sensor 112 does not encounter any intermediate optical component on its way. In some embodiments and as will be explained below, a structured light transparency may be disposed between light emitters 118 and projecting microlens 120. However, in some embodiments, a structured light pattern may be printed on light emitters 118 and/or projecting microlens 120 negating the use of a structured light transparency.

One or more micro light emitters 118 may be disposed within head 150 and deep to projecting microlenses 120 disposed within apertures 122. As will be explained in greater detail below, a projection microlens 120 may be an array of projection microlenses, one example of which is microlens 120 array of projection microlenses depicted in the example of FIG. 8.

Optionally, IOS 100 may include an elongate element 108 optionally fixedly, optionally removably or optionally movably coupled to a first surface 106 of intraoral scanner (IOS) 100 facing a region of interest (ROI). Elongate element 108 may be angled in respect to first surface 106, optionally, extending generally normal to surface 106.

In FIG. 1, elongate element 108 is disposed in the center of surface 106. Optionally, elongate element 108 may be off-centrally disposed on surface 106. Elongate element 108 may be shaped as a stylus and have a diameter between 0.05-2.0 mm, optionally between 0.1 and 1.5 mm less than 0.05 mm or more than 2.0 mm.

Elongate element 108 may have a length measured from surface 106 between 1 and 25 mm, optionally between 2 and 20 mm, less than 1 mm or more than 25 mm. Optionally, elongate element 108 may be telescopic and may vary in length as required. Additionally and optionally elongate element 108 has a rounded or balled tip to be disposed against a tooth or oral tissue for stability.

Implementation of Scanner Optics in an IOS

The implementation of scanner optics described hereinbelow described using microimages and microlenses, which are components manufactured mainly by wafer level technology (see reference to FIG. 8 below) may not necessarily require use of miniaturized optical IOS components (e.g., wafer level imagers and light emitters, flat lenses and similar) and can be carried out employing commonly used suitably sized IOS components. The combination of the below described optical solutions and wafer level IOS components may contribute in concert to downsizing an IOS head.

Adaptation and modification of scanner optics may contribute to downscaling the IOS form factor. Processor 116 processing operation includes analysis of the properties of an acquired image at any specific point in time and under a given set of conditions at that specific point in time. Optical acquisition parameters and other parameters affecting the acquired image properties are also optionally integrated into the image processing operation and are adjusted in accordance with output from processing unit 116. Acquisition parameters may include spatial orientation of IOS head 150 in respect to an ROI, projected light parameters (number of light emitters, light intensity, coherence or non-coherence, wavelength, pulsed or continuous, pulse frequency, projected structured light pattern and others), direction and rate of IOS movement, focal length, FOV size, distance between ROI and imager and/or light emitter and more.

Figure 2B:
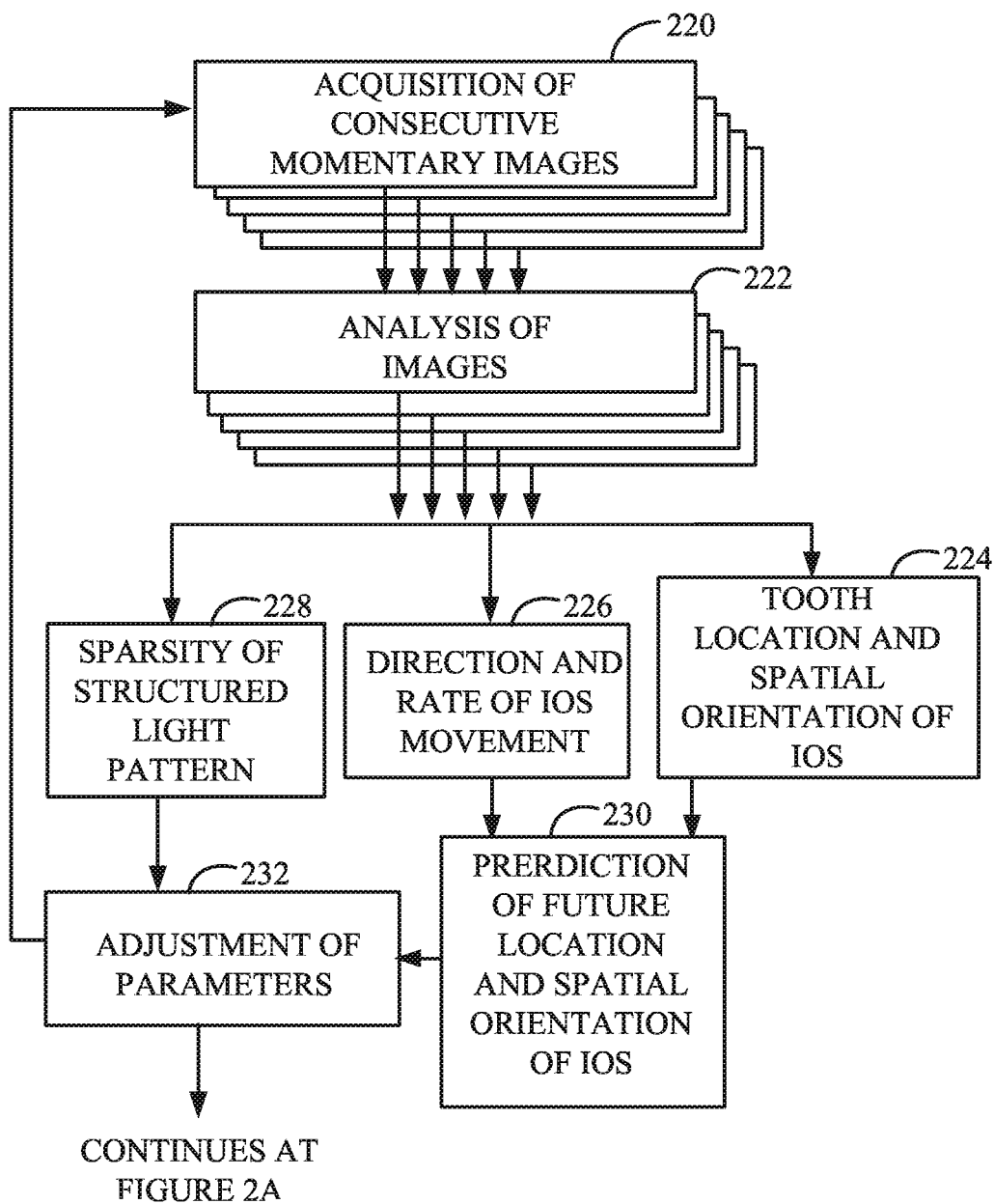

FIGS. 2A and 2B are exemplary flow charts of a processing unit 116 processing operation of an image acquired by IOS head 150. In FIG. 2A at 202 IOS 150 acquires a momentary image of a FOV of a ROI and communicates the acquired image by wire or wirelessly to processing unit 116. Analysis of the acquired image at 204 results in a depth image 206 of the FOV that provides ROI (e.g., tooth) location and spatial information of the imaged ROI such as depth, angles, hills and valleys, etc. as well as the spatial orientation of the IOS at 208 in respect to the imaged ROI.

At 210, FOV image properties such as, for example, image resolution, contrast, brightness, and/or color profile, etc. are extracted from the image analysis at 204. At 212, processor 116 receives analysis of image properties at 210, ROI (e.g., tooth) location and IOS spatial orientation in respect to the ROI at 208 and determines if any parameters require adjusting e.g., selection of a specific light emitter 118, brightness of projected light, etc. need to adjusted. If yes-processing unit 116 or IOS 150 circuitry signaled by processing unit 116 make the necessary adjustment at 214 based on the processing operation and inputted information at 216 of location of light emitters 118 and imagers 112 on IOS head 150. Adjustment at 214 may also include adjustment of IOS head 150 spatial orientation such as angularity in respect to ROI. This can be done manually by alerting the operator or automatically. Another momentary image is acquired and the process repeated. If at 212 no optic adjustments are required, at 218 the data resulting from the processing is outputted to the 3D model. All data analyzed at 212, including partial or incomplete information, may be outputted for construction of a 3D model. Optionally, at 204 analysis can include only image properties analysis 210 or depth analysis 206.

FIG. 2B illustrates processing of acquired images during movement of IOS head 150. At 220 and 222 a plurality of momentary consecutive images are acquired and analyzed similarly to steps 202 and 204 of FIG. 2A. The analysis at 222 provides at 224 the ROI (e.g., tooth) location and IOS spatial orientation in respect to the ROI at the corresponding acquisition time of the analyzed image, at 226 the direction and rate of IOS head 150 movement and at 228 the sparsity and required filling of the structured light pattern if such a pattern is cast on the ROI. The resulting data extracted from 224 and 226 provides at 230 means for prediction of future location and spatial orientation of IOS head 150 in respect to the current ROI. Processor 116 may also determine future necessary adjustments of IOS head 150 image acquiring parameters.

At 232, data from 230 regarding prediction of future location and spatial orientation of IOS head 150 may be combined with information from 228 regarding sparsity of a structured light pattern (if cast) and at 232 processing unit 116 adjusts or signals IOS head 150 circuitry to adjust parameters (e.g., light projection parameters). Adjustment at 232 may also include adjustment or change of structured light pattern as well as IOS head 150 spatial orientation such as angularity in respect to ROI. This can be done manually by alerting the operator or automatically. From step 232, processing continues back to step 202 of FIG. 2A and/or step 220 and repeated.

Adjustment of illumination of a light pattern projected on a region of interest (ROI) (steps 214, 232) may include in some instances, adjustment of the angle of incidence of projected light onto the scanned surface. The angle of incidence of the projected light may be detrimental to the accuracy of 3D information derived from the acquired image. For example, light incident on an axial surface of a tooth at too high an angle may result in a blurred or "smudged" image. This, commonly results from the returned light being far from the source of light or the perspective view of a striped light pattern viewed by the imager that may exhibit itself, for example, as having decreased distances between stripes. Light incident onto an axial surface of a tooth at generally a large angle in respect to normal an axial surface may, in some instances, contribute to the quality of the acquired image. In some instances, the tooth location in the image can be identified by the color of the tooth (e.g., to differentiate the tooth from gingival tissue) to determine the angle of incidence of projected light onto the scanned tooth.

Acquired image properties may be affected by the physiological or anatomical characteristics of the oral cavity. One example may be specular reflection from a tooth. As described above, in some systems powder is applied to the teeth in an attempt to achieve sharp and uniform reflectance of light and to provide texture to the surface of the tooth. However, the amount of an applied powder layer may be difficult to control resulting at times in excessive and/or non-uniform powder layer thickness resulting in reduction in accuracy of the constructed model as well as excessive stages and time for the IOS user.

In some embodiments processing unit 116 may identify, for example, a first region in the acquired image that is saturated due to specular reflection and select or signal IOS head 150 circuitry to turn off or dim the current active first light emitter and activate a second light emitter that illuminates a second region of the ROI (or same region) with a different incidence angle eliminating the specular reflection affecting the acquired image transferring the light saturation to a second region of the ROI. In some embodiments, a plurality of light emitters 118 can be alternately selected and activated so that to alternate between zones with specular reflection and zones free of specular reflection and acquire specular reflection free images. Similarly, a plurality of image sensors 112 may be used alternatively to acquire specular reflection free images. A combination of alternating image sensors 112 and light emitters 118 may also be used to produce specular reflection free zones in the ROI.

FIG. 3, which is a cross-section view simplified illustration of an example of implementation and adjustment of scanner optics, depicts intraoral scanner (IOS) head 150 scanning an axial surface or wall 202 of a tooth 300. Micro light emitters 118, 318 emit light through projecting microlenses 120 and 320 respectively that illuminates axial surface 202 of tooth 300. For purposes of simplification of explanation reference numeral 330 indicates a point of interest (POI) within a field of view (FOV) 332 of image sensor 112. A plane (Q) is tangent to axial surface 202 at POI 330 and normal to, extending in and out of, the surface of the paper. In the example of FIG. 3, light incident on surface 202 at POI 330 at an angle normal to plane Q tangent to POI 330 would be considered to produce optimal illumination conditions. In this example, the closer to normal the incident light may be the acquired image will have better properties such as, for example, clarity, contrast, speckle, visible light structure stripes or lines, etc.

As shown in FIG. 3, light incident on axial surface 202 POI 330 originating from light emitter 118 via projecting microlens 120, a general direction thereof indicated by arrow 350, is incident on axial surface 202 at an angle (a) from plane (Q). Light incident on axial surface 202 POI 330 originating from light emitter 318 via projecting microlens 320, a general direction thereof indicated by arrow 370, is incident on axial surface 202 at an angle (B) from plane (Q). As shown in FIG. 3, angle (a) is greater than angle (B) and closer to normal in respect to plane (Q) than angle (B).

Processor 116 may acquire and process images of FOV 332 communicated thereto by wire or wirelessly and illuminated by light emitter 118 as well as images of FOV 332 illuminated by light emitter 318 or a combination of illumination by both projectors 118, 318 or by any other combination of illumination. Based on the processing, processor 116 may, for example, activate light emitter 118 only; activate light emitter 118 and dim light emitter 318 or any other combination to provide the best possible 3D image of POI 330. In the example of FIG. 3, processing may indicate that projector 118 is optimal at the specific point in time and location of POI 330, angle of incidence (a) being closest to normal, i.e., between 30 and 90 degrees from a plane (Q) and thus activate or signal IOS head 150 circuitry to activate light emitter 118 only. Optionally, the angle of incidence may be between 40 and 80 degrees, optionally between 50 and 70, less than 50 degrees or more than 70 degrees.

The angles of incidence of emitted beams can be determined using 3D location and angles of tooth and other measured oral feature in respect to known IOS micro projector and/or imager locations.

In an example depicted in FIG. 4, which is a cross-section view simplified illustration of an example of implementation and adjustment of scanner optics, IOS head 150 may include one, two or more image sensors 112, 412 and imaging lenses 110, 410 respectively imaging respective FOVs 434, 436. For purposes of simplification of explanation reference numeral 438 indicates a region of interest (ROI) on a tooth 400 within fields of view (FOV) 434, 436 of image sensors 112, 412 respectively. ROI 438 is generally planar defining a plane (Q) normal to, extending in and out of the surface of the paper. In the example of FIG. 3, a light beam incident on and illuminating a largest portion of surface 202 ROI 438, mainly along the axial dimension thereof would be considered to produce optimal illumination conditions.

As shown in FIG. 3, a light beam projected by light emitter 118 via projecting microlens 120 has a beam angle ($\gamma$). A light beam projected by light emitter 418 via projecting microlens 420 has a beam angle ($\theta$). As shown in FIG. 3, beam angle ($\gamma$) is greater than angle ($\theta$) and is incident on a larger portion of surface 202 ROI 438, mainly along the axial dimension thereof. Processor 116 may acquire and process images of FOVs 434 and 436 communicated thereto by wire or wirelessly and illuminated by light emitter 118 as well as images of FOV 436 illuminated by light emitter 418 or a combination of illumination by both projectors 118, 418 or by any other combination of illumination. Based on the processing, processor 116 may, for example, activate light emitter 118 only; activate light emitter 118 and dim light emitter 418 or any other combination to provide the best possible 3D image of ROI 438.

Alternatively and optionally, based on the processing, processor 116 may, for example, activate image sensor 112 only and turn off image sensor 412, activate both image sensors 112 and image sensor 412 and process a combination of images acquired from both or employ any other combination of light emitters 118, 418 and image sensors 112, 412 to provide the best possible 3D image of ROI 438. In the example of FIG. 3, processing may indicate that projector 118 is optimal at the specific point in time, size and location of ROI 438, having a largest beam angle and illuminating a largest portion of ROI 438, mainly in the axial dimension thereof and thus activate or signal IOS head 150 circuitry to activate light emitter 118 and/or image sensor 112 only. The illuminated portion along the axial dimension of the ROI may be between 30-100 percent, optionally between 50-80 percent and optionally between 60-70 percent of the axial dimension of the ROI.

Figure 5A:
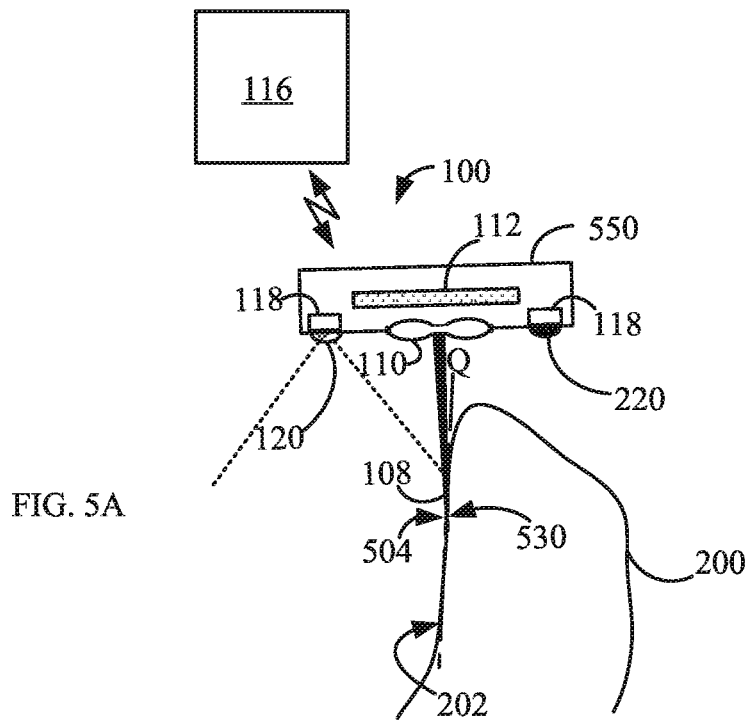
FIGS. 5A and 5B are cross-section and plan view simplified illustration of an example of implementation of scanner optics in accordance with embodiments of the current invention.
Figure 5B:
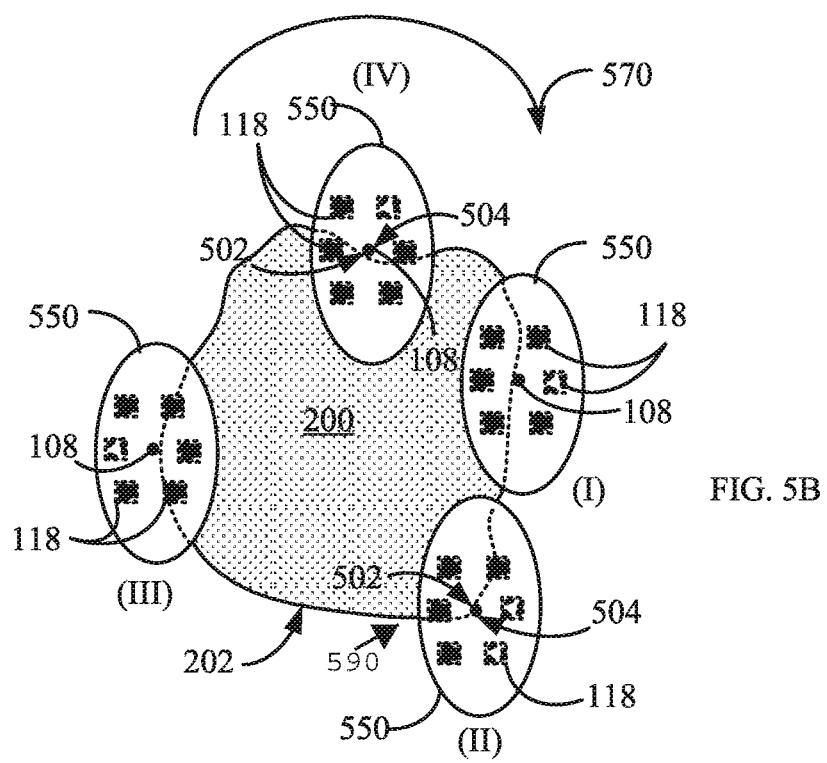

Reference is now made to FIGS. 5A and 5B, collectively referred to as FIG. 5, which are a cross-section view and top view simplified illustrations of an example of implementation and adjustment of IOS head 150 scanner optics. Circumferential scans are prevalent 3D mapping techniques of a tooth. As depicted in the example of FIG. 5, intraoral scanner (IOS) 100 includes an elongate element 108 in a form of a stylus. A plane (Q) is tangent to axial surface 202 at point of contact (POC) 530 and normal to, extending in and out of the surface of the paper.

In the example depicted in FIG. 5A, IOS 100 head 550 is positioned over tooth 200 with at least a portion 502 of element 108 in contact with axial surface 202. One or more images acquired through imaging microlens 110 and projected onto image sensor 112 may be communicated by wire or wirelessly to processing unit 116 for processing as explained hereinabove. Based on the processing of the received image or images of the ROI, processing unit 116 may automatically select and activate or signal IOS head 150 circuitry to adjust IOS optics such as, for example, to activate one or more of the plurality of micro light emitters 118 projecting light via projecting microlenses 120, 220 the light beam of which is incident on a non-contacting portion of a surface 504 of element 108. Optimally, non-contacting portion 504 is close to opposite to portion 502 in contact with axial surface 202.

Processing unit 116 may adjust IOS head 150 optics by, for example, turning off or signaling IOS head circuitry to turn off non-selected micro light emitters as indicated in FIG. 5A by a blackened microlens 220. Light incident on non-contacting portion of a surface 504 of element 108 optimally close to opposite to portion 502 in contact with axial surface 202 also incidents onto an axial surface 202 of a tooth in contact with element 108. Optionally, processor 116 may also select an imager 112 on the same side of the non-contacting portion 504 of element 108 not in contact with axial surface 202 of tooth 200. Element 108 may not necessarily be in contact with an axial surface of a tooth and may be in contact with any surface of the tooth.

FIG. 5B illustrates the process of micro light emitter selection by processing unit 116 described in reference to FIG. 2B as IOS 100 head 550 is moved along a circumference of a tooth 200 in a direction indicated by an arrow designated reference numeral 570. As described in FIGS. 2B and 5A above, processing unit 116 may automatically select and activate or signal IOS head 150 circuitry to activate one or more of a plurality of micro light emitters 118 the light beam of which is incident on a portion 504 of element 108, optimally, close to opposite to portion 502 of a surface of element 108 in contact with axial surface 202. For example, processor 116 may determine which of emitters 118 is between element 108 and the ROI. Optionally one or more of those emitters 118 is deselected and/or deactivated. For example, processor 116 may determine which of emitters 118 are positioned such that element 108 is between emitter 118 and the ROI. Optionally one or more of those emitters 118 are selected and/or activated. For example, processor 116 may determine which of sensors 112 is between element 108 and the ROI. Optionally one or more of those sensors 112 is deselected and/or deactivated. For example, processor 116 may determine which of sensors 112 are positioned such that element 108 is between sensors 112 and the ROI. Optionally one or more of those sensors 112 are selected and/or activated.

In some embodiments, elongated element may contact a ROI in a hidden location, for example under a gum line. Optionally, processor 116 determines an orientation of element 108 with respect to the ROI and/or an orientation of IOS head 550 with respect to the ROI and/or element 108. In some embodiments, based on the relative orientation of head 550, element 108 and/or the ROI, processor 116 selects and/or actives a sensor 112 and/or a light emitter 118 that will produce an image from which the 3D location of the point of contact between element 112 and the ROI can be determined that will produce an image from which the 3D location can be determined more accurately. Alternatively or additionally, processor 116 deselects and/or deactivates a sensor 112 and/or a light emitter 118 that will not produce an image from which the 3D location of the point of contact between element 112 and the ROI can be determined and/or that will produce an image from which the 3D location can be determined less accurately. Optionally, processor 116 predicts a future relative orientation of head 550, element 108 and/or the ROI. Optionally the selected deselecting and/or adjusting is based on the predicted future orientation.

As shown in FIG. 5B elongate element 108 of IOS head 550 in position (I) is in contact with an axial surface or wall 202 of tooth 200. Processing unit 116 may then select one or more micro light emitters 118 (indicated in FIG. 5B by a whitened micro light emitter (118) the light beam of which incident non-contacting portion 504 of element 108. Processing unit 116 may also turn off or dim non-selected micro light emitters as indicated in FIG. 5B by blackened micro light emitters 118.

As IOS head 550 is moved into position (II), the light beam of microlight emitter activated previously at position (I) is still incident on non-contacting portion 504 of element 108 as does a light beam emitted from an adjacent micro light emitter 118. Hence, both light emitters are selected and activated by processing unit 116 or IOS head 150 circuitry. In IOS head 550 at position (III), light from micro light emitters 118 previously activated in position (II) is no longer incident on non-contacting portion 504 of element 108 and they are turned off. A single micro light emitter 118 located on the opposite side of IOS head 150 is then selected and activated. In IOS head 550 at position (IV) once again the micro light emitter 118 previously activated in position (III) is now turned off or dimmed. An adjacent micro light emitter 118 the light beam of which is now incident on a portion 504 of element 108 optimally opposite to portion 502 of a surface of element 108 in contact with axial surface 202, which was previously [positions (I) through (III)] off is now selected and activated. Selection and deselection of light emitters to be activated can be done in quick succession while IOS head 550 is moved along the circumference of tooth 200 as described in reference to FIG. 2B.

Optionally, at position II, upon acquiring a momentary image of tooth 200 and based on previous consecutive acquired images, processing unit 116 may predict the direction and rate at which IOS head 150 is being moved as well as an expected turn around bend 590 in tooth 200 axial wall as explained in reference to FIG. 2B above.

Structured Light Projection

In some embodiments, depth information can be obtained from a projected structured light pattern cast on a ROI and using at least one optical aperture. For example, U.S. Provisional Patent Application No. 61/745,744 filed 24 Dec. 2012 the contents of which are incorporated herein by reference in their entirety teaches how to take sub-gingival measurements and/or intraoral measurements. A user can use any type of pattern projection and any type of 3D reconstruction, for example, as known in art of IOS.

If a portion of a pattern is imaged through at least two apertures the differences between the two pattern images can be used to obtain depth information using stereo view or multi-view. In some embodiments of the invention optimization of an imaged tooth acquisition includes casting structured light onto the surface of the imaged tooth or ROI. The topography of the ROI deforms the cast pattern and the deformed image may be then acquired and communicated to processing unit 116 that processes the acquired image and extracts depth information therefrom.

The confined space in the oral cavity one example of which is the posterior area of the dental arcade, may at times set constraints that limit the ability to project a high quality structured light pattern, for example, casting structured light onto the imaged tooth from too high an angle resulting in, for example, crowding of projected stripes and/or low contrast of the structured light pattern reducing depth measurement accuracy.

Similarly to the described in reference to FIGS. 2A, 2B, 3 and 4, in some embodiments processing unit 116 may process an acquired structured light image and based on the processing automatically select and activate or signal IOS head 150 to activate one or more of the plurality of structured micro light emitters the structured light pattern of which produces the highest image quality (e.g., sparsity, contrast and resolution).

Referring back to FIGS. 1 and 3-5A-B, in some embodiments IOS 100 head 150 may include a plurality of image sensors 112. In some embodiments, a plurality of image sensors 112 may be dispersed about elongate element 108 coupled to IOS head 150 surface 106. In some embodiments, each image sensor of a plurality of image sensors 112 may be coupled to a micro light emitter 118. In some embodiments, a plurality of image sensors 112 may be dispersed about a single micro light emitter 118. In some embodiments based on acquired image(s) processing unit 116 may automatically select and activate or signal IOS head 150 circuitry to activate one or more of image sensors 112 that receive an image from an imaging microlens 110 on which a light beam reflected from axial surface 202 incidents at an angle close enough to normal to a ROI on axial wall 202.

Figure 6:
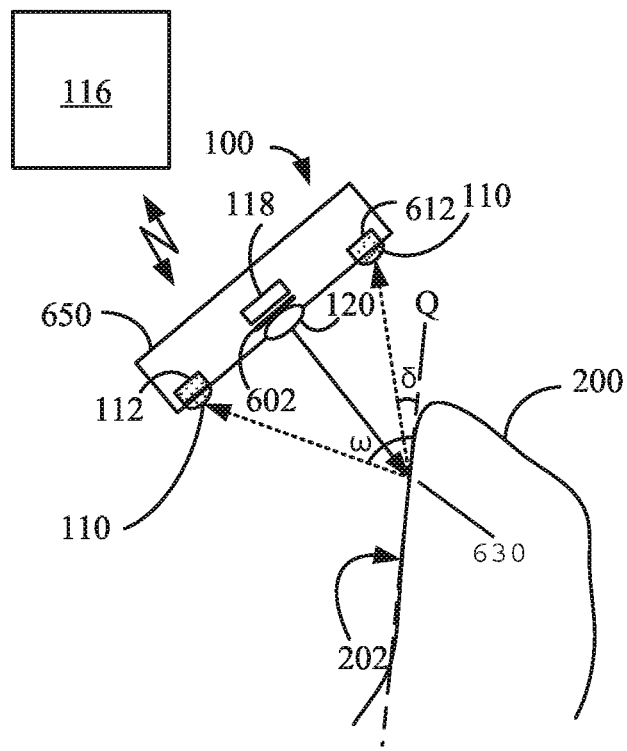
FIG. 6 is a cross-section view simplified illustration of an example of implementation of scanner optics in accordance with embodiments of the current invention.

In some embodiments and as shown in FIG. 6, which is a cross-section view simplified illustration of an example of implementation and adjustment of scanner optics, head 650 of IOS 100 may include a plurality of image sensors 112, 612 and a micro light emitter 118 that may projects light through a structured light micro transparency 602 and cast structured light via projecting microlens 110 onto an axial surface or wall 202 of scanned tooth 200.

In some embodiments, a smaller micro lens array can replace micro transparency 602 and including a structured light pattern mask to improve efficiency of production and reduction in cost. In some embodiments, the microprojector can include a diffractive optical element (DOE). In some embodiments, projecting lens 120 includes a structured light mask imprint or markings and projects structured light onto the surface of the ROI. Only a single light beam is illustrated in FIG. 6 for purposes of simplifying the explanation. A plane (Q) is tangent to axial surface 202 at POI 630 and normal to, extending in and out of, the surface of the paper.

Processing unit 116 may process a received structured light image of imaged tooth 200 as previously described in reference FIGS. 2A and 2B and based on the processing may automatically select one or more of the image sensors 112, 612 that acquires the most accurate image information (e.g., a light beam of an image incident on imaging microlens 110 reflected off axial surface 202 at an angle optimally normal to plane (Q).

In the example of FIG. 6, reflection angle ($\omega$) of the beam incident on image sensor 112 microlens 110 is greater than reflection angle ($\delta$) of the beam incident on image sensor 612 microlens 110. Hence, processing unit 116 may select image information received from image sensor 112 over image information received from image sensor 612, angle (ω) being closer to normal to plane (Q) than angle (δ). Alternatively and optionally, processing unit 116 may select a combination of image sensors 112, 612 or a combination of image sensors 112, 612 and light emitter or projectors 118.

Figure 7A:
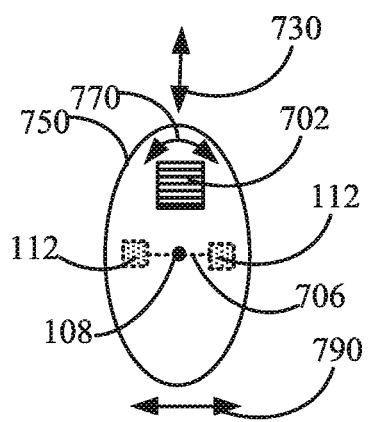
FIGS. 7A, 7B and 7C are plan view simplified illustration of an example of implementation of scanner optics in accordance with embodiments of the current invention.
Figure 7B:
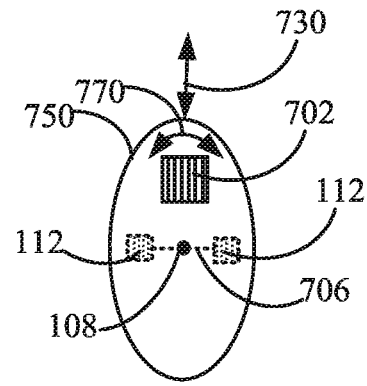

Reference is now made to FIGS. 7A, 7B and 7 (', collectively referred to as FIG. 7, which are bottom view (viewed from the direction of the ROI) simplified illustrations of examples of implementation and adjustment of IOS structured light optics. In FIG. 7, some IOS head components have been removed for purposes of simplifying the explanation. FIG. 7A depicts an embodiment of an IOS head 750 having two image sensors 112 and a structured light projecting microtransparency 702 that projects a structured light pattern (not shown) onto a ROI.

In the example of FIG. 7, structured light projecting microtransparency 702 is rotatable about an axis normal to first surface 106 of IOS head 750 as indicated by a doubled headed arrow 770. Structured light projecting microtransparency 702 may be rotatable manually or automatically by processing unit 116 in which case the rotation of projecting microtransparency 702 in respect to IOS head 750 may be synchronized in correlation with the direction of movement of IOS head 750.

In FIG. 7, projecting lens 120 has been removed to reveal the schematically shown structured light pattern represented several lines of magnified structured light transparency 702. In some embodiments instead of rotating microtransparency 702, a spatial light modulator can be used such as used for mobile microprojectors, for instance transmissive or reflective (LCOS) micro displays or DMD or MEMS scanned mirror based microprojectors.

In the example of FIG. 7A, the structured light pattern is constructed of schematically drawn parallel lines, parallel to a baseline 706 connecting the center of optical image sensors 112 and normal to the direction of movement of IOS head 750 as indicated by an arrow 750. In this case, depth information can be obtained from the variations of a projected pattern over several images obtained by image sensors 112. Since the pattern lines are, in general, parallel to baseline 706 of image sensors 112 the variations of the projected lines in the two respective acquired images caused by depth variations will be similar in both sensors 112. However, other oral or teeth features will vary between the two acquired images and their depth information can be obtained using stereo vision.

The depth information obtained using structured light and stereo or multiview of oral features can be combined at processing unit 116. Additionally, in this configuration movement of IOS head 750, while scanning the tooth in the direction indicated by arrow 730 will bring about filling of information gaps resulting from the structured light pattern sparseness and increase the density of obtained depth surface by combining many sparse depth images of the pattern lines into a single dense depth surface at processing unit 116 increasing depth data resolution and a more accurate 3D image(s) and measurement. In some embodiments the pattern orientation of FIG. 7A can be used, for example, for scanning with IOS head 750 up and down in directions indicated by double headed arrow 790, in coronal and apical directions along an axial wall of a prepared tooth.

The schematic structured light line pattern projected by structured light projecting microtransparency 702 shown in FIG. 7B is rotated by 90 degrees in respect to the pattern shown in FIG. 7A so that the lines projected by structured light projecting microtransparency 702 are now normal to baseline 706 connecting the center of image sensors 112. In this configuration, depth information can be obtained from the variations of the projected pattern between the images obtained through image sensors 112. Since the pattern lines are in general normal to baseline 706 between optical image sensors 112 the variations of the projected lines in the two respective acquired images caused by depth variations will be opposite for each image sensor 112.

Depth information obtained using structured light and stereo or multiview of oral features can be combined at processing unit 116. In this configuration, movement of IOS head 750 in the directions indicated by double headed arrow 730 will almost not improve the sparseness of the structured light pattern and thus not contribute to resolution of the acquired image(s).

However, scanning around the tooth circumference and turning IOS head 150 along the circumference of the tooth will bring about filling of information gaps resulting from the structured light pattern sparseness and increase the density of obtained depth surface by combining many sparse depth images of the pattern lines into a single dense depth surface at processing unit 116 increasing depth data resolution and a more accurate 3D image(s) and measurement. This combined with the above described in reference to FIGS. 5A-B and 6 may lead to an increase in the density of the obtained depth surface by combining many sparse depth images of patterned lines into a single dense depth surface at processing unit.

In some embodiments, the pattern orientation may be correlated with the IOS scanning direction. For example, the above described use of the pattern of FIG. 7A to scan an axial surface of a tooth in apical and coronal directions or, optionally, using the pattern of FIG. 7B orientation for scanning with IOS head 750 around a prepared tooth, such as described and depicted in reference to FIGS. 5A-B and 6, together with processing unit 116 selecting and activating the proper micro light emitter 118 and projecting lens 120 which provide the optimal pattern direction according to scanning direction of the user.

In some embodiments processing unit 116 selecting and activating the proper micro light emitter 118 and projecting lens 120 which provide the optimal pattern direction according to scanning direction of the user as well as optimal scanning angle in respect to the axial surface of a tooth while scanning around the circumference of the tooth.

In FIG. 7O, structured light projecting microtransparency 702 is rotated to project a schematic line pattern of diagonal lines that are close to normal to baseline 706 connecting the centers of image sensors 112. In this example, variations of projected pattern or lines during movements will be different between the two images acquired by image sensors 112. These differences in pattern line variations can be used for removing or reducing depth ambiguities, e.g., in cases in which periodical or repetitive patterns are used.

Figure 7C:
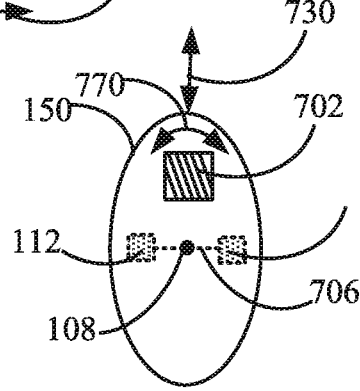

The configuration of FIG. 7C has similar advantages to those of the configuration of FIG. 7B, for example, for scanning with IOS head 750 around a prepared tooth. This, combined with the above described in reference to FIGS. 5A-B, may lead to an increase in the density of obtained depth surface by combining many sparse depth images of patterned lines into a single dense depth surface at processing unit. Depth information obtained using structured light and stereo or multiview of oral features can be combined at processing unit.

In some embodiments several structured light projecting slides 702 with several pattern orientations can be used to cast patterns on a common portion of the ROI, so that processing unit 116 can select the most appropriate structured light projecting microtransparency 702 to use based on IOS head 750 orientation and position in respect to the location of tooth 200 and/or ROI and that provides best angle of view as described hereinabove to support high density depth image acquisition. In some embodiments, plurality of projectors can be activated simultaneously, wherein each projector has a different color and the relevant imagers are color imagers.

Utilization and optimization of scanner optics contributes to contrast, resolution depth accuracy and robustness of the acquired image and allows for use of smaller IOS components such as wafer level micro light emitters, microlenses and image sensors and nullifies the need for components such as, for example, mirrors, reflectors, optic fibers, beam splitters and other image relaying components between an end optical element (e.g., imaging lens) and image sensor or between micro light emitter and end optical element (e.g., projection lens) thus contributing to low form factor of the IOS.

Structure and Positioning of Scanner Components in an IOS

Figure 8:
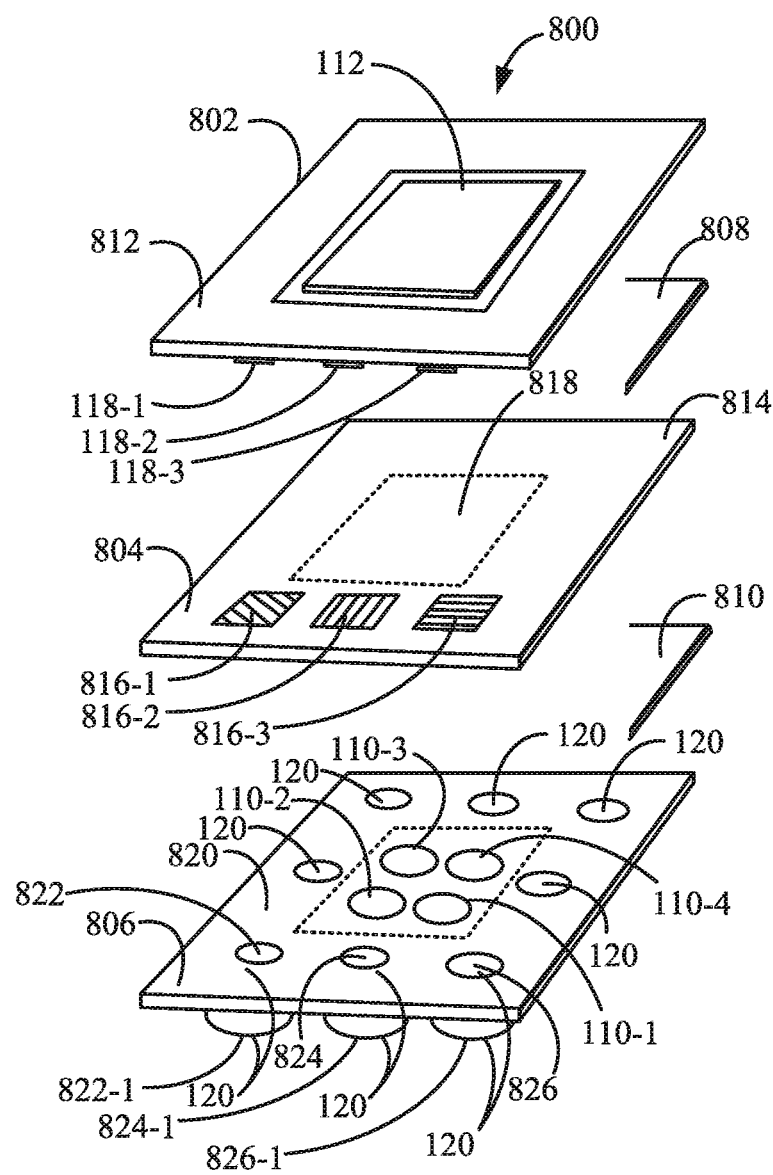
FIG. 8 is an exploded view simplified illustration of IOS 100 optical transmitters/receivers WLO module in accordance with embodiments of the current invention.

Reference is now made to FIG. 8, which is an exploded view simplified illustration of an example of an IOS 100 optical transmitters/receivers WLO module 800. WLO module 800 may be constructed as a multi-layered module the layers of which may be mechanically attached, manufactured together or bonded to each other in the final production step as wafers or at least some or all as diced elements or isolated elements. In the example depicted in FIG. 8, WLO module 800 includes three layers 802, 804 and 806 optionally separated by two spacer frames 808 and 810. Layer 802 may include an image sensor 112 or an array of image sensors 112 the imaging face thereof facing layer 806. Image sensor 112 may be a semiconductor charge-coupled device (CCD), a complementary metal-oxide-semiconductor (CMOS) or a similar type of optical sensor.

Optical sensor 112 may be framed by a light emitter 118 frame 812. Frame 812 may include a plurality of light emitters 118 facing in the same direction as image sensor 112 (e.g. the beam direction of emitters 118 is approximately parallel to the viewing direction of sensors 112), emitting light in the direction of layer 806. Three light emitters 118-1, 118-2 and 118-3 are visible in FIG. 8. Frame 812 can be made of PCB or Si wafer with mounted light emitters 118. Light emitters may be at least one of a Surface-Mounted-Device Light-Emitting Diode (SMD LED) Module, a Chip on Board (COB) LED, A multi-COB (MCOB), an edge emitting Laser, a vertical-cavity surface-emitting laser (VCSEL) or any similar suitable light emitter. Light emitters 118 can be packaged with or without a diffusing surface. Optionally, sensors 112 and/or emitters 118 are mounted with their optical apertures approximately along a plane. For example, the plane may be approximately perpendicular to the average beam direction of emitters 118 and/or the average viewing direction of sensors 112. For example, where the viewing direction and beam direction of each sensor 112 and/or emitter 118 are all approximately parallel, then the average direction is approximately parallel to all of the viewing directions and/or beams. For example, lines connecting the optical apertures of the components may all be within 0-2 degrees and/or 2-5 degrees and/or 5-10 degrees of perpendicular to the average beam direction of emitters 118 and/or the average viewing direction of sensors 112.

Layer 802 may be attached to spacer frame 808, which may or may not include optical elements such as condensing and/or diffusing elements under light emitters 118 (not shown). Spacer frame 808 may be attached to a glass wafer 814 that includes a plurality of structured light pattern transparencies 816, each corresponding to a light emitter 118. Three light pattern transparencies 816-1, 816-2 and 816-3 are shown in FIG. 8 corresponding to light emitters 118-1, 118-2 and 118-3. Structured light patterns 816 can be produced for example, with chrome lithography. Glass wafer 814 may also include a clear portion 818 corresponding the image receiving area of image sensor 112. Clear portion 818 may also be coated with a filtering coat, such as IR cut filter, spectral filters, AR coating, filter pixels, CMOS regions or any other suitable coat.

Glass wafer 814 may be attached to spacer frame 810, which in turn may be attached to layer 806. Layer 806 may be an integral microlens wafer 820 including micro optics image microlenses 110, projection lenses 120 and other suitable optical elements.

Additionally, fabrication of the above described WLO module 800 may provide better mechanical stability of the baseline between the projectors and image sensors which may result in acquisition of more accurate depth information and lower sensitivity to temperature and mechanical shocks (e.g., trauma to the IOS, IOS falling to the floor and similar). In some embodiments if the bond between image sensor and imaging lens in the image acquisition modules or bonded arrays is sufficiently accurate—baseline calibration may be unnecessary. Optionally, better mechanical stability can be achieved if WL microlenses technology is based on glass e.g., in glass molded array or polymer lenses on glass wafer.

Quality production of different types of microlens arrays on the same wafer contributes to efficiency of production and lowers production cost especially at mass production.

In the example of FIG. 8, microlens wafer 820 includes elements 822, 822-1; 824, 824-1 and 826, 826-1, each pair may be disposed on both sides of lens wafer 820 forming a projection microlens 120. Projection microlenses 120 can be made of a polymer or any other suitable clear material. The location of projection microlenses 120 may correspond to light pattern transparencies 816-1, 816-2 and 816-3 and light emitters 118-1, 118-2 and 118-3. Lens wafer 820 may also include a plurality of imaging microlenses 110 that correspond to segments of the pixel area of image sensor 112. Four imaging microlenses 110-1, 110-2, 110-3 and 110-4 in four apertures are shown in FIG. 8. Additional wafers with optical elements such as microlens wafer 820 with or without spacer frames can be added to improve optical quality. In addition, optical apertures for said lenses can be added on wafer 820, such as using chrome lithography or on additional wafer.

Microlenses 110 and 120 as well as well as image sensor 112 can be produced by parallel batch processing to cut costs. Parallel batch processing also enables the shrinkage of the imaging optics array track length contributing to miniaturization of the IOS head. In the example of FIG. 8, image microlenses 110 and projection 120 may be manufactured on the same array and bonded to an array of light emitters 118 and image sensor 112.

Manufacturing can include state-of-the-art micro-optical, WLO fabrication techniques. A total track length may be, for example, 1.4 mm, which is about half the length of comparable single-aperture optics on image sensors of the same pixel pitch.

Limiting the size of image acquisition modules, as explained in reference to FIG. 8, may provide the freedom to select a desired field of view(s) (FOV) that will provide the most precise information for processing unit 116 to reconstruct the most accurate 3D model from an acquired image. Do to their small size, such modules may be positioned about anywhere along surfaces of the IOS so that the user/processing unit 116 may select image acquisition modules that are most suitable at a certain point in time for generating a specific 3D image.

FIGS. 9A, and 9B, which are cross-section view simplified illustrations of embodiments of IOS head 150. In the embodiments of FIGS. 9A and 9B IOS head 950 includes one or more optic transmitters/receivers WLO modules 800-1 disposed on a first surface 906 facing a first region of interest (ROI). In FIGS. 9A and 9B, some IOS head components have been removed for purposes of simplifying the explanation. Additionally and optionally, IOS head 950 may also include one or more second surfaces 914 facing a second and third region of interest (ROI). One or more second surfaces 914 may be angled in respect to first surface 106, mutually forming a convex third surface 920 each including one or more optic transmitters/receivers WLO modules 800-2.

In FIGS. 9A and 9B, convex third surface 920 is U-shaped. Each of first surface 906 and one or more second surfaces 914 respective optic transmitters/receivers WLO modules 800-1/800-2 may be disposed on convex third surface 920. Optionally, one or more optic transmitters/receivers WLO modules 800-3 may be disposed on a fourth surface 930, opposite to surface 906 and facing away from the first ROI. One or more optic transmitters/receivers WLO modules 800-3 on surface 930 may provide additional information for processing unit 116 regarding the location in the oral cavity and spatial orientation of IOS 100. Optionally, one or more optic transmitters/receivers WLO modules 800-3 on surface 930 may also allow an operator to select an upper jaw or lower jaw to be scanned without flipping IOS head 150 over or both jaws can be scanned simultaneously. Selection of FOV on either side of IOS head 150 can be done by manual or automatic selection.

In the example of FIG. 9A, the FOVs of One or more optic transmitters/receivers WLO modules 800-1, 800, 2800 do not overlap. Optic transmitters/receivers WLO modules 800-2 may provide image information of additional FOVs over the scanned tooth and/or other oral features supporting and contributing to image information acquired by optic transmitters/receivers WLO modules 800-1.

The information obtained from optic transmitters/receivers WLO modules 800-2 may assist in processing of the spatial orientation and position of IOS head 950 in the oral cavity. The FOVs of optic transmitters/receivers WLO modules 800-2 can be equal in size. Optionally and alternatively, the FOVs of optic transmitters/receivers WLO modules 800-2 can differ in size. In some embodiments, for example, the FOV of optic transmitters/receivers WLO modules 800-1 can be larger than the FOVs of optic transmitters/receivers WLO modules 800-2, e.g., the size ratio between the FOV of optic transmitters/receivers WLO modules 800-1 and the FOVs of optic transmitters/receivers WLO modules 800-2 may be 1.5:1; 2:1; 2.5:1; 3:1 or larger or smaller. In the example illustrated in FIG. 9B, FOVs of optic transmitters/receivers WLO modules 800-2 and 800-1 overlap and thus provide an extended single FOV from which spatial reference can be derived.

Reference is now made to FIG. 10, which is a cross-section view simplified illustration of an embodiment of IOS head. The IOS head may include a single image sensor 112, a plurality of light emitters disposed on IOS head first and second surfaces 1006, 1014 respectively facing a first, second and third region of interest (ROI) respectively. First and second surface 1006, 1014 may each include at least one image acquisition lens 1002. Optionally, lens 1002 is manufactured by wafer level optics (WLO) technology and/or includes an optical transmitter/receiver wafer level optics (WLO) module 1010. Light incident on one or more image acquisition lenses 1002 disposed on first surface 1006 travels directly to and is incident on a first portion of image sensor 1012 pixel area. Light incident on one or more image acquisition lenses 1002 disposed on second surfaces 1014 travels to image sensor 1012 via one or more mirrors or prisms 1004 an is incident on a second and third portions of image sensor 1012 pixel area.

In the embodiment of FIG. 10, image sensor 1012 receives three images at one, each representative of a unique field of view (FOV) providing processing unit 116 information regarding IOS location in the oral cavity as well as IOS orientation in reference to a desired ROI (e.g., a tooth). Additionally, information received from each imaging lens 1002 complements and supports information received from the other imaging lenses 1002. The arrangement shown in FIG. 10 is compact thus supporting downscaling IOS head 150 by employing a single image sensor for acquiring several separate unique images.

Reference is now made to FIG. 11, which is a plan view and cross section view thereof at level C-C simplified illustration of an embodiment depicting implementation of optimization of positioning of scanner components. In FIG. 11, some IOS head components have been removed for purposes of simplifying the explanation. IOS head 1150 may include image acquisition modules 1102, 1104, 1106, 1108, 1112, 1114, 1116, 1118 and light emitting modules 1120 arranged about elongate element 108. Optionally and alternatively, the FOVs of image acquisition modules 1104, 1106, 1114 can be equal in size. Optionally, image acquisition modules 1102, 1104, 1106, 1108, 1112, 1114, 1116, 1118 may share the same image sensor employing spate lenses (not shown).

Optionally and alternatively, the FOVs of image acquisition modules 1104, 1106, 1114 can differ in size. In the embodiment of FIG. 11, image acquisition modules 1102, 1104, 1106, 1108 may have a standard FOV, e.g., between 30-90 degrees, optionally between 40-80 degrees, optionally between 50-70 degrees, less than 50 degrees or more than 70 degrees, whereas image acquisition modules 1112, 1114, 1116, 1118 may have an extra-wide FOV, e.g., between 80-160, optionally between 90-150 degrees, optionally between 100-140 degrees, less that 100 degrees or more than 140 degrees. In some embodiments, for example, the FOV of image acquisition module 1114 can be larger than the FOVs of image acquisition modules 1104, 1106, e.g., the size ratio between the FOV of image acquisition module 1114 and the FOVs of image acquisition modules 1104, 1106 may be 1.5:1; 2:1; 2.5:1; 3:1 or larger or smaller.

In the example illustrated in FIG. 11, FOVs of image acquisition module 1114 includes FOVs of image acquisition modules 1104, 1106 however, the focal length of image acquisition module 1114 may be different from the focal length of image acquisition modules 1104, 1106. For example, the ratio between the focal length of image acquisition module 1114 and focal lengths of image acquisition modules 1104, 1106 may be 1.5:1; 2:1; 2.5:1; 3:1 or larger or smaller.

This FOV combination supports acquisition of a high resolution image of an ROI (e.g., tooth) from the generally relatively narrower FOV image acquisition modules 1102, 1104, 1106, 1108 and better pose estimation using the wide angle FOV image acquisition modules 1112, 1114, 1116, 1118. The pose estimation may be needed for stitching depth images obtained at each frame into a single 3D model. Pose estimation can be obtained using algorithms such as structure from motion or bundle adjustment of all inputs obtained from all image acquisition modules or using sensors accelerometer, gyro, compass etc.

Optimization of Scanner Components

IOS 100 is a downscaled multiaperture optics digital intraoral scanner (IOS) having a small form factor. In some embodiments head 150 houses all components necessary to generate a three dimensional (3D) image and measurement data sufficient to at least prepare a tooth prosthetic fitted to the tooth axial surface above and below the gingival border (gum line). This so that to shorten "communication lines" between IOS components by nullifying the need for mirrors, reflectors and other image relaying components and bring the various optic components (e.g., micro light emitters and sensors) as close as possible to the ROI so that to increase accuracy and precision of acquired 3D information. Additionally to utilization of IOS optics to reduce the form factor of IOS head 150, utilization of scanner component optics to reduce IOS head 150 form factor may also contribute to achieve the desired down-sizing of IOS 100 and especially head 150.

In some embodiments image sensor 112 is a semiconductor charge-coupled device (CCD), or such as a complementary metal-oxide-semiconductor (CMOS), with or without a color filter array (CFA) such as, for example, a RGB Bayer Filter or a similar type of optical sensor. In some embodiments image sensor 112 may acquire a single image projected onto its entire active pixel area. In some embodiments, a portion of image sensor or at least one of image sensors does not include CFA to improve sensitivity and a portion of image sensor or at least one of image sensors include CFA for providing color information of oral features and projected pattern.

In some embodiments, image sensor 112 may acquire a plurality of overlapping images projected onto its entire active pixel area. In some embodiments image sensor 112 may acquire a plurality of images each projected by an individual imaging microlens 110 or imaging microlens element onto a corresponding segment or fraction of image sensor 112 active pixel area. In some embodiments image sensor 112 can be formed be an array of image sensory elements formed on a wafer. In some embodiments, a plurality of image sensors 112 may be disposed deep to IOS head 150 first surface 106 about elongate element 108.

In some embodiments, imaging microlenses 110 may be segmented or fractionized, manufactured by WL optics technology using semiconductor-like techniques that produce an array of optical elements. In some embodiments a plurality of imaging microlenses 110 are manufactured as an array of imaging microlenses 110. In some embodiments, an array of imaging microlenses 110 may be manufactured together with and bonded to a layered plurality of image sensors 112. In some embodiments an image sensors wafer may be diced together with the imaging microlens 110 array to provide individual image acquisition modules each including at least one imaging microlens 110 attached to one image sensor 112.

In some embodiments image sensor 112 and imaging microlens 110 array may not be diced and fitted as such in IOS 100 head 150. In some embodiments, WL microlenses may be made of metamaterials.

In some embodiments imaging microlenses 110 may be attached to a plurality of image sensors 112 using mechanical alignment. In some embodiments, imaging microlenses 110 may be bonded to a plurality of image sensors 112 and be aligned using active alignment. In some embodiments the imaging microlens 110 array may be bonded to a single image sensor 112. In some embodiments, the imaging microlens 110 array may be a glass-molded array. In some embodiments, the imaging microlens 110 array may be made of polymer microlenses on a glass support (e.g., UV molding of microlenses and application of cured polymer on glass wafers). In some embodiments, imaging lenses 110 may be made by other microlens array fabrication methods known in the art.

In some embodiments, projection microlenses 120 may be produced as a WL projection microlens array in an above described fashion similar to that of imaging microlenses 110 array. In some embodiments, an array of projection microlenses 120 may be manufactured together with and bonded to one or more micro light emitters 118 to form light emitting modules.

In some embodiments light emitters 118 may be micro optics light emitter such as, for example, a Surface-Mounted-Device Light-Emitting Diode (SMD LED) Module, Chip on Board (COB) LED, multi-COB (MCOB), Laser and vertical-cavity surface-emitting laser (VCSEL).

In some embodiments image sensor 112 may acquire image segments in which the imaging microlenses create a number of non-overlapping microimages on the image sensor active pixel area. The microimages represent part of the total FOV. Processing unit 116 may digitally or optically stitch the image segments (microimages) received from the image sensor to combine the received images and generate a single image of the FOV. This supports use of WL microlens arrays having a relatively narrow field of view (FOV). In some embodiments, multi-aperture optics may increase the effective imaging by having each WL microlens array segment project a low-resolution image of the full FOV on the image sensor. Processing unit 116 may then analyze the received images to create the final image of high resolution from all partial images (e.g., super resolution techniques).

In some embodiments, multi-aperture optics may increase effective 3D image acquisition by having each WL microlens array segment project an image of the full FOV on the image sensor, each image taken at a slightly different angle (shift). Processing unit 116 may then analyze the received images to create the final 3D image from all partial images.

Reference is now made to FIG. 12, which is a cross-section view simplified illustration of an embodiment of a multiaperture optics intraoral scanner (IOS), shows an IOS head 1250 including one or more color image acquisition modules 1202 (for instance, CMOS with RGB Bayer filter) and diffractive optic element (DOE) 1204 receiving one or more laser beams from one or more laser source 1206 in one or more wavelengths. In some embodiments, DOE 1204 may also include a collimating effect cone and a diffraction grating to create light stripes. In the embodiment of FIG. 12, laser source 1206 generates three laser beams at RGB wavelengths via a single optical fiber 1214 to DOE 1204 that casts a pattern 1210 on a ROI (e.g., tooth) 1212. In accordance with the grating equation [$\sin(\theta)=m\lambda/d$] the diffracted light pattern depends on its wavelength hence various portions of cast pattern 1210 will be modulated by a wavelength of the light beam creating the respective portion.

The RGB cast pattern forms three individual patterns each at one of the RGB wavelengths and the refracted patterns reflected off ROI 1212 may be acquired by one or more RGB image acquisition modules 1202 and communicated to processing unit 116. Processing unit 116 may process the acquired RGB patterns, for example, to solve ambiguity issues. Use of laser produced RGB wavelength light structured image may contribute to a low cost small form factor easily maneuverable instrument inside the oral cavity and comfortable for the patient.

In another embodiment, IOS head 150 may include at least one monochrome image sensor and at least one color image sensor both having the same FOV including a projected color structured light image. In this configuration, the monochrome and colored image sensors complement each other to provide an accurate acquired image at processing unit 116, the monochrome image sensor having a high sensitivity (approximately 3 times higher sensitivity than the color image sensor) and the color imager may be employed to prevent cross talk at the processing unit 116 level.

Other form of utilization of scanner component optics to reduce IOS head 150 form factor may also optionally include addition of mirrors to fold an optical path in instances in which imagers and/or projectors have a longer equivalent focal length (EFL). Optionally, different imagers may have different EFL to support different magnifications. Optionally, different imaging lenses may have different focal distances thus improving depth of the FOV. Optionally, imagers may be allotted different exposure times (by a processing unit) or include variable apertures to provide a better high dynamic range (HDR).

Figure 13:
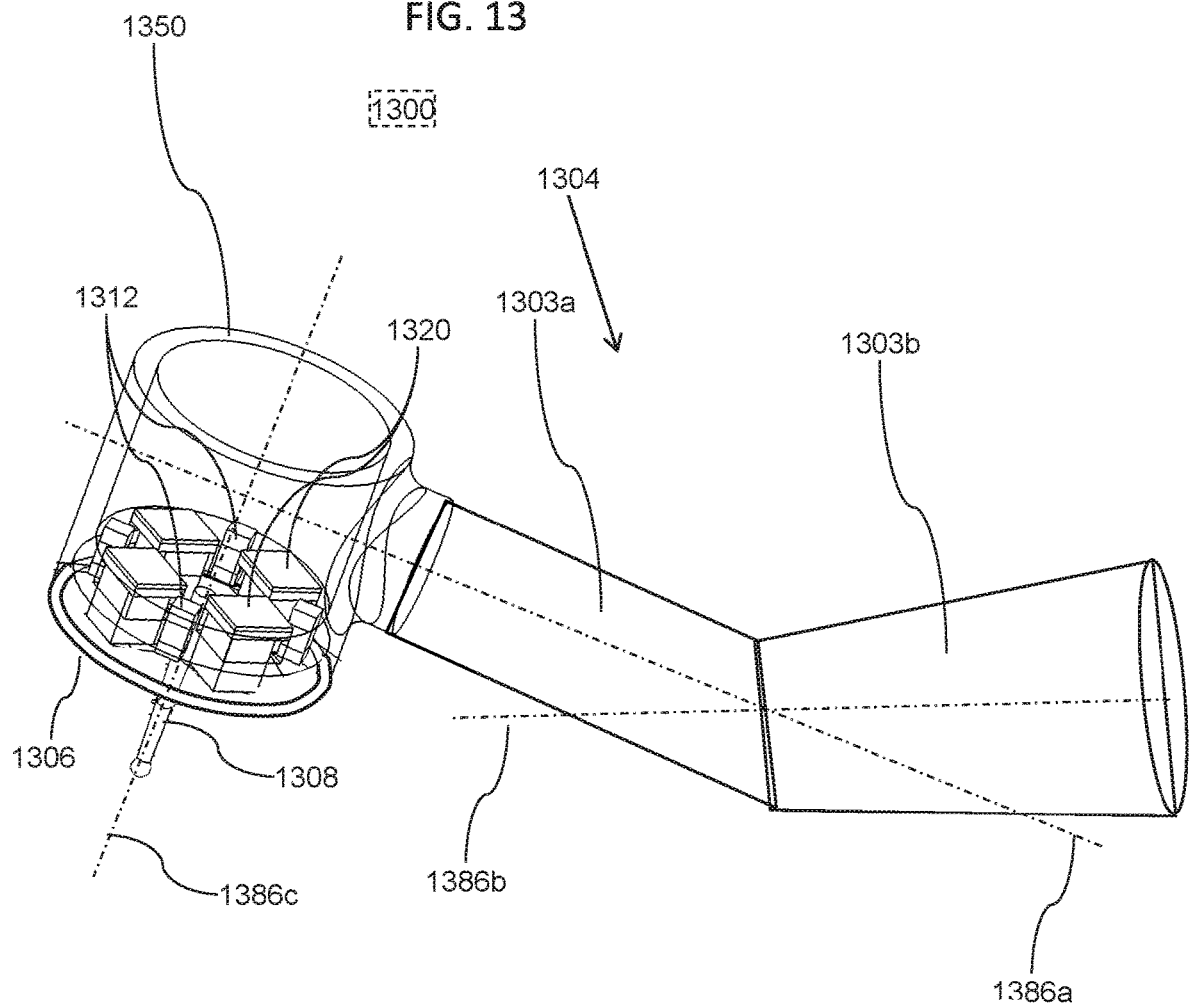
FIG. 13 is a perspective view simplified illustration of an embodiment of an IOS tool in accordance with embodiments of the current invention.

FIG. 13 illustrates an IOS scanner in accordance with an embodiment of the current invention. In some embodiments, an IOS scanner will be included in a tool having a form familiar to many dentists. For example, the IOS may be mounted on a tool shaped like a dental drill. Alternatively or additionally, the IOS may be mounted on a dental tool, for example a drill and/or probe.

In some embodiments, an IOS 1300 may include two or more sensor modules 1312 and/or two or more light emitters 1320. Optionally the sensor modules 1312 (for example image sensor) and/or light emitters 1320 (for example emitters and/or pattern projectors) may be combined together in a small form factor dental tool 1300. For example, dental tool 1300 may be shaped as a dental drill. For example, turbine shaped intraoral scanner 1300 includes four image sensor modules 1312, four light emitters 1320, a probe 1308 and/or a handle 1304. In some embodiments handle 1304 is angled similar to angled handles of some of dental turbines. Optionally a device may include between 1 to 4 sensor modules and/or between 5 to 10 sensor modules and/or more sensor modules. Optionally a device may include between 1 to 4 emitters and/or between 5 to 10 emitters and/or more emitters. Optionally the mean viewing direction of sensor modules 1320 and/or the mean beam direction of emitters 1320 is approximately parallel to an axis 1386c of the scanning head and/or approximately perpendicular to a surface 1306 facing a ROI. Optionally the mean viewing direction of each sensor module 1320 and/or the mean beam direction of each emitter 1320 are approximately parallel to each other and/or approximately parallel to the axis 1386 of the IOS head and/or approximately perpendicular to a surface 1306 facing a ROI.

In some embodiments, multiple sensor modules 1312 and/or emitters 1320 may be arranged on an IOS head 1350. For example, sensor modules 1312 and/or emitters 1320 may be arranged around probe 1308. For example, various emitters may include pattern generators having similar and/or different patterns and/or may have similar or different frequencies and/or orientation. For example, various sensor modules may include similar and/or different properties. Optionally a single sensor and/or emitter may be selected and/or activated to capture a desired view of a ROI. Alternatively or additionally, multiple sensors and/or emitters may be selected and/or activated together and/or serially to capture a multiple views of a ROI.

In some embodiments probe 1308 is linear. Optionally an axis of probe 1308 is approximately parallel to an axis 1386c of IOS head 105. Alternatively or additionally probe 1308 may not be straight. For example 1308 probe may be curved, bent and/or angled. Optionally a probe may include proximal end contacting the IOS head and/or a distal end opposite the proximal end. Optionally, the probe may include a distal portion next to the distal end and/or a proximal portion next to the distal end. Optionally the mean direction of the distal portion and/or the proximal portion may be parallel to axis 1386c of IOS head 1305. Optionally the distal portion and or the proximal portion may be linear.

In some embodiments, optical components (for example sensor modules 1312 and/or light emitters 1320) may be supported with their optical apertures on a single depth and/or on multiple depths with respect to a surface 106, 1306 facing a ROI, and or with respect to a viewing axis. For example, multiple sensor modules 1312 may have their optical aperture on a plane parallel to surface 106, 1306. This may, for example, facilitate acquiring multiple views of a single ROI. Optionally, an optical aperture of emitters 1320 may be on the same plane as sensor modules 1312. In some embodiments, viewing angles of multiple sensor modules 1312 may vary. In some embodiments, viewing angles of multiple light emitters 1320 may vary. In some embodiments, the length of components may vary. For example, the length of sensors 1312 may differ from the length of emitters 1320. Optionally, a compensation feature may align the optical apertures of components of different lengths. For example, for components mounted on a PCB, a compensation layer may lift short components off the face of the PCB and/or a flexible PCB may be flexed to align components and/or multiple rigid PCB's may be placed at different heights. Optionally multiple PCB's may be interconnected. Alternatively or additionally, individual components may be mounted separately at a desired height from a surface. In some embodiments, optical apertures may be mounted at a determined depth from a surface at an angle to the surface. For example, the components may be mounted to and/or positioned with respect to surface 106, 1306 facing the ROI and/or with respect to a curved surface and/or an angled surface.

In some embodiments, handle 1304 may include a distal portion 1303a and/or a proximal portion 1303b. For example, proximal portion 1303b may be adapted for handling by a dentist and/or distal portion 1303a may be adapted for insertion into the mouth of a patient. For example, the length of distal portion 1303a may range between 0 to 1 cm and/or between 1 cm to 3 cm and/or between 3 cm to 6 cm and/or between 6 cm to 20 cm. For example, the length of proximal portion 1303a may range between 0 to 5 cm and/or between 5 cm to 10 cm and/or between 10 cm to 20 cm and/or between 20 cm to 100 cm. In some embodiments an axis 1386a of distal section 1303a and an axis 1386b of distal section 1303b may form an angle ranging between 0 to 10 degrees and/or between 10 to 30 degrees and/or between 30 to 60 degrees. In some embodiments, an axis 1386c of IOS head 1350 and an axis 1386b of distal section 1303b may form an angle ranging between 90 to 80 degrees and/or between 80 to 60 degrees and/or between 60 to 30 degrees. It is understood that angular relationships recited herein also apply to elements that are parallel to a recited element and/or apply with a 90 degree rotation to elements that are perpendicular to a recited element.

In some embodiments, an array of components may be supported with optical apertures at different heights from a surface. For example, the optical apertures of multiple sensor modules may be fixed at different depths with respect to surface 1306. In some embodiments, varying the depths of the optical aperture may increase a depth of field focus of the array. Alternatively or additionally, components having different focal lengths may be mounted at a single depth from surface 1306, for example to increase a depth of focus and/or components having different focal lengths may be mounted at a differing depth from surface 1306 to synchronize their focal length and/or get multiple views of a single ROI and/or the depth of a component with respect to surface 1306 may be adjusted according to its distance from a center of focus, for example to compensate horizontal position along plane 1306, for example to facilitate focus of multiple components onto a single point.

Figure 14:
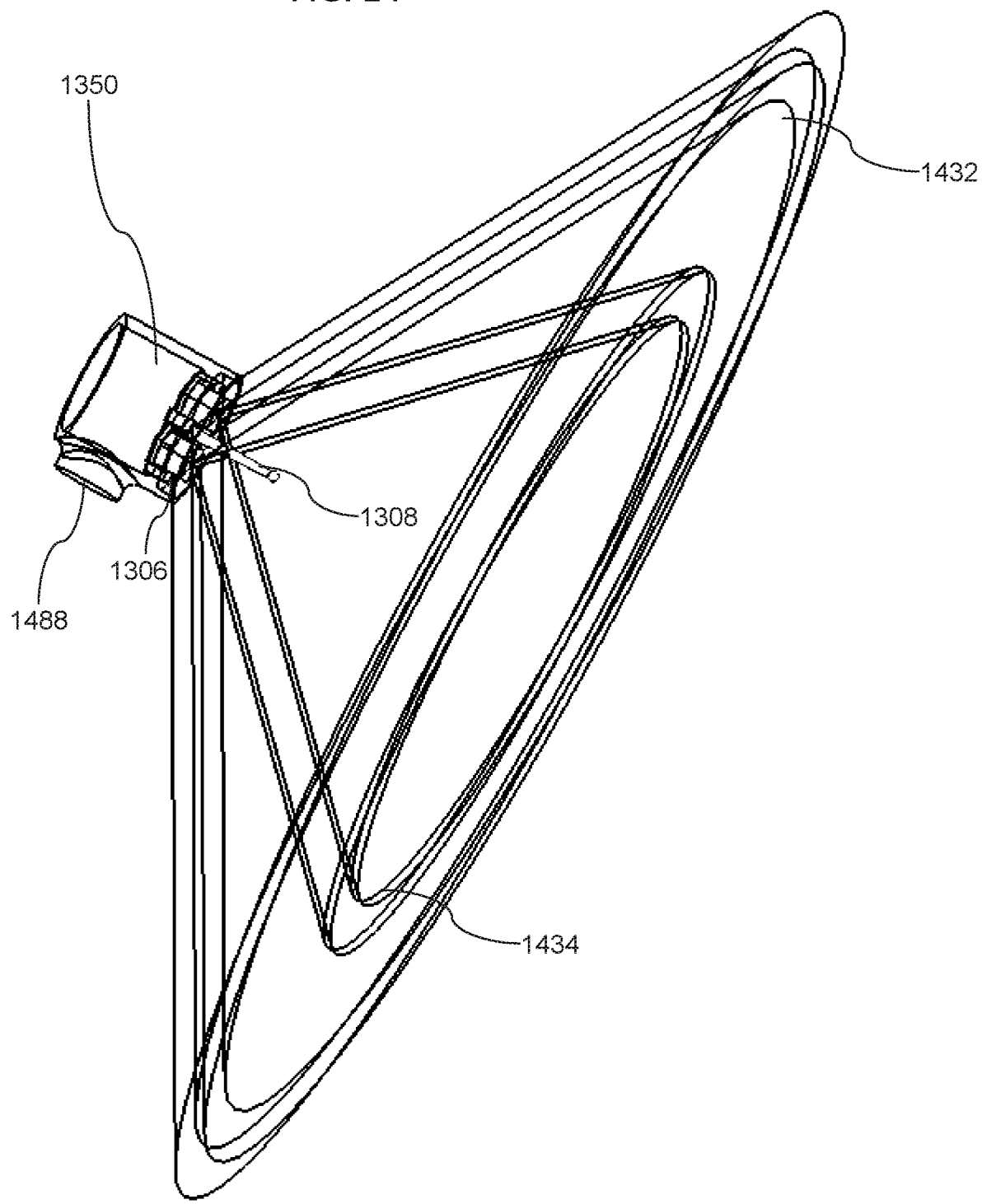
FIG. 14 is a perspective view simplified illustration of an embodiment of an IOS head in accordance with embodiments of the current invention.

FIG. 14 illustrates overlapping sensor module FOV's 1434 and/or light emitter FOV's 1432. Optionally, FOV's 1432, 1434 of various components (for example sensor modules 1312 and/or emitters 1320) may overlap and/or cover separate areas. Optionally, FOV's 1432, 1434 of various components may have a similar focal length and/or differing focal lengths. For example, illustrated FOV's 1434 of various sensor modules 1312 partially overlap. For example, illustrated FOV's 1432 of various emitters 1320 partially overlap. Optionally, FOV's 1432 of emitters 1320 surround FOV's 1434 of various sensor modules 1312. Alternatively or additionally, FOV's of emitters may partially surround FOV's of various sensor modules and/or be surrounded by FOV's of various sensor modules. IOS head 1350 includes an optional mount 1488. For example, mount 1488 may be configured to connect head 1350 to handle 1304.

In some embodiments, an IOS head (for example head 1350) may be mounted on a dental tool. For example, an annular IOS head may be mounted to a dental drill. Optionally while a dentist is working the drill, the IOS head may be making images of a ROI.

In some embodiments, an IOS tool shaped as a dental tool may include a various other components and/or functionalities for example as described herein above. For example, the IOS device may include a built in processor and/or communicate with an external processor. For example, the processor may analyze an image and/or adjust parameters of the IOS. For example, locations of projectors and/or imagers may be adjusted over time according to a position and/or movement of the IOS with respect to an ROI.

FIGS. 15*a-c* and 16*a-c* illustrate various geometries of synchronized components and/or mounts. For example, various examples of staggered mounts are illustrated. In some embodiments, staggering components may align and/or disalign optical apertures. For example, the components may be mounted on staggered boards such as staggered rigid interconnected PCB's, a flexible PCB and/or a PCB with spacers.

Figure 15A:
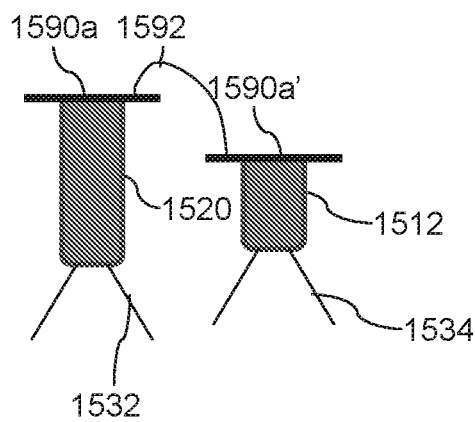
FIG. 15A illustrates an exemplary way to align optical apertures in accordance with embodiments of the current invention; particularly, a long and a short component may be mounted with aligned optical apertures using separate PCBs.
Figure 16A:
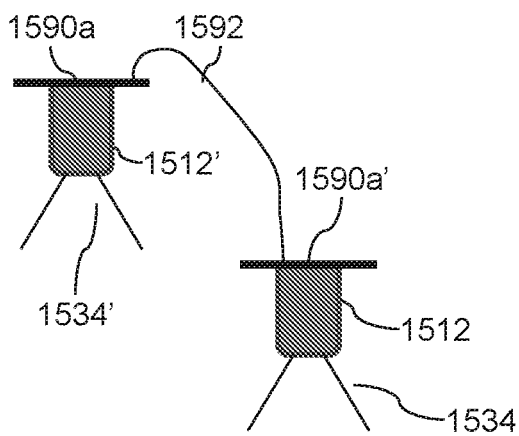
FIG. 16A illustrates an exemplary way to align optical apertures in accordance with embodiments of the current invention.

In some embodiments (for example as illustrated in FIG. 15*a*) a long and a short component may be mounted with aligned optical apertures using separate PCBs. For example, a long light emitter 1520 and a short sensor module 1512 are mounted on separated PCB's 1590*a* and 1590*b* such that their optical apertures and/or FOV's 1532 and 1534 respectively are aligned, for example on a single plane. Optionally, PCB's 1590*a* and 1590*a'* are interconnected by a connector, for example a cable 1592.

Figure 15B:
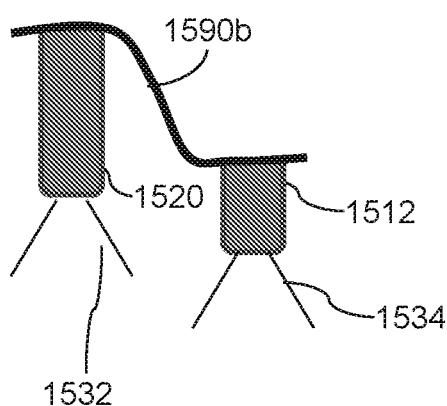
FIG. 15B illustrates an exemplary way to align optical apertures in accordance with embodiments of the current invention; particularly, mounting two components with disaligned optical apertures using separate PCBs.
Figure 16B:
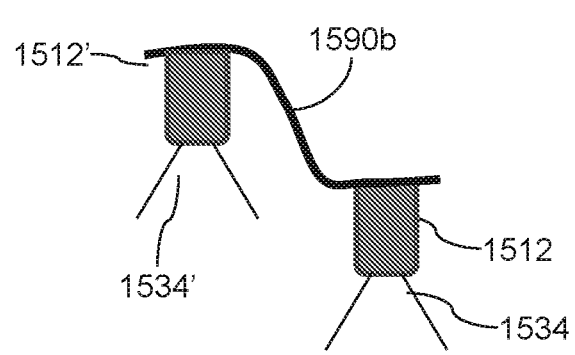
FIG. 16B illustrates an exemplary way to align optical apertures in accordance with embodiments of the current invention; particularly, two similar components are mounted on a single rigid PCB.
Figure 15C:
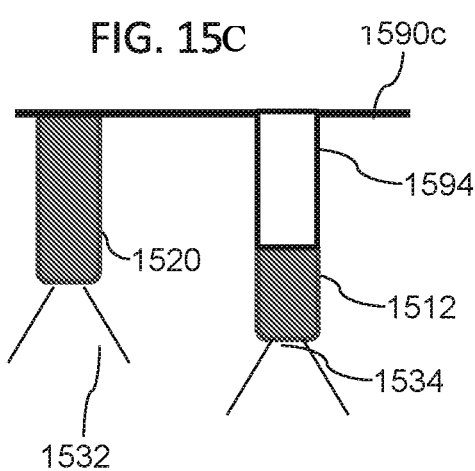
FIG. 15C illustrates an exemplary way to align optical apertures in accordance with embodiments of the current invention; particularly, a long component and a short component are mounted on a single rigid PCB.
Figure 16C:
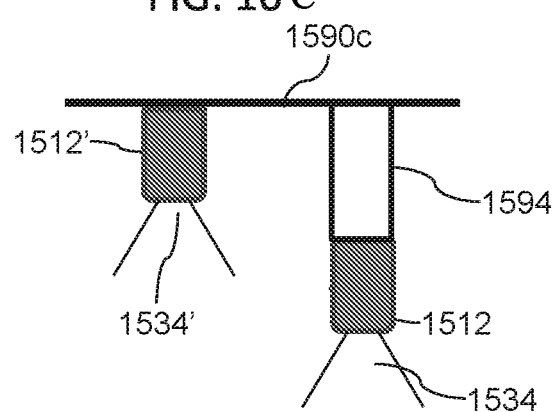
FIG. 16C illustrates an exemplary way to align optical apertures in accordance with embodiments of the current invention.

FIG. 15*b* illustrates mounting two component with disaligned optical apertures using separate PCBs. Optionally two similar sensor module 1512, 1512' are mounted on separated PCB's 1590*a* and 1590*b* such that their optical apertures and/or FOV's 1534 and 1534' respectively are disaligned, for example on separate planes. For example, such a geometry may be used to increase a focal length of a sensor array. For example, sensor 1512' will focus on a POI near the IOS device while sensor 1512' will focus on a POI further from the IOS device.

In some embodiments, FOV's be aligned and/disaligned using a flexible PCB. For example in FIG. 15*b*, a long component (for example emitter 1520) and a short component (for example sensor module 1512) are mounted on a single flexible PCB 1590*b*. Optionally, the optical apertures and/or FOV's 1532 and 1534 are aligned by bending flexible PBC 1590*b*. For example in FIG. 16*b* two similar components (for example sensor modules 1512 and 1512') are mounted on a single flexible PCB 1590*b*. Optionally, the optical apertures and/or FOV's 1534 and 1534' are disaligned by bending flexible PBC 1590*b*.

In some embodiments, FOV's be aligned and/or disaligned using a spacer. For example in FIG. 15*c*, a long component (for example emitter 1520) and a short component (for example sensor module 1512) are mounted on a single rigid PCB 1590*c*. Optionally, the optical apertures and/or FOV's 1532 and 1534 are aligned by mounting the smaller component on a spacer 1594. For example in FIG. 16*b* a two similar components (for example sensor modules 1512 and 1512') are mounted on a single rigid PCB 1590*c*. Optionally, the optical apertures and/or FOV's 1534 and 1534' are disaligned by mounting module 1512 on spacer 1594.

Figure 17:
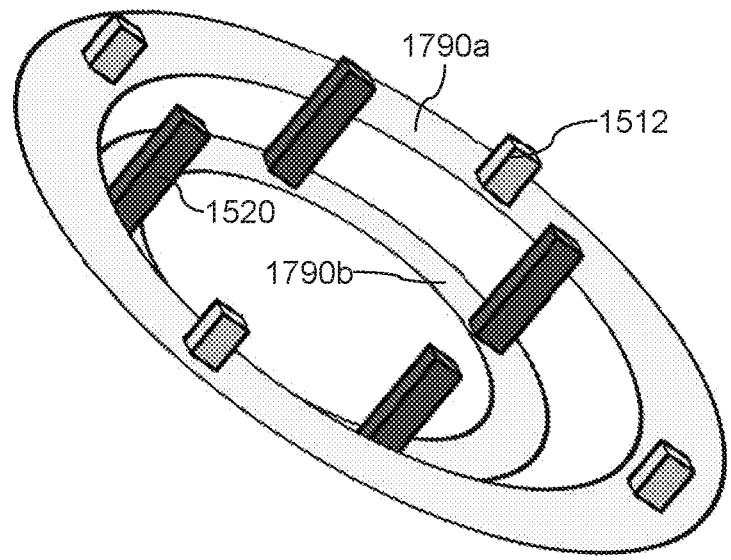
FIG. 17 illustrates staggered mounting of arrays of aligned optical components of a IOS in accordance with embodiments of the current invention.
Figure 18:
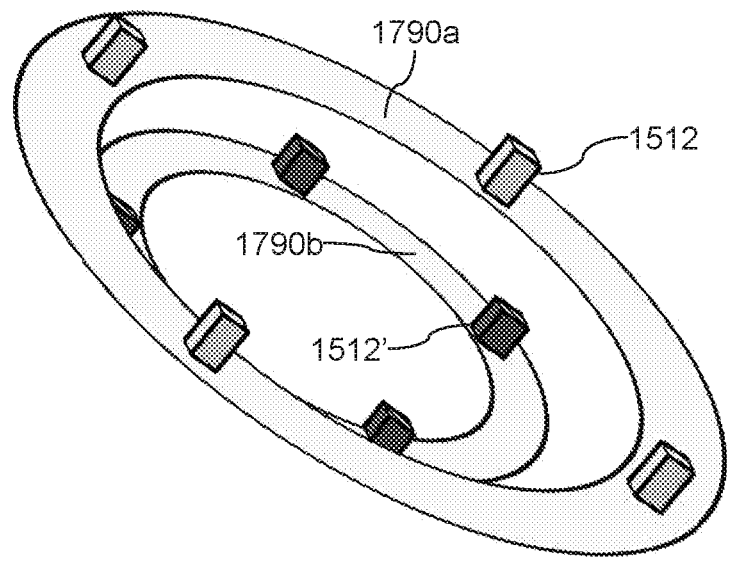
FIG. 18 illustrates staggered mounting of arrays of disaligned optical components of a IOS in accordance with embodiments of the current invention.

FIGS. 17 and 18 are illustrations of staggered arrays of sensor modules 1512 and/or emitters 1520. For example, FIG. 17 illustrates aligning optical apertures of an array of different sized emitters 1520 and sensors modules 1512 on staggered mountings 1790*a*, 1790*b*. For example, FIG. 18 illustrates disaligning optical apertures of an array of similar sized sensors modules 1512 and 1512' on staggered mountings 1790*a*, 1790*b*. Alternatively or additionally, mixed arrays of different and/or similar sized components may be may be aligned and/or disaligned. For example, FIGS. 17 and 18 illustrate concentric circular arrays of components. Alternatively or additionally, linear arrays may be staggered (for example like steps) and/or in other shaped arrays (for example rectangular and/or pentagonal and/or hexagonal). Optionally staggered arrays may be concentric and/or arranged as steps and/or in another geometry.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An intraoral scanner (IOS) comprising:
   a. one or more image sensors; and
   b. one or more structured light projectors;
      wherein some image sensors from said one or more image sensors and some structured light projectors from said one or more structured light projectors are formed on one or more interconnected boards;
      wherein some image sensors from said one or more image sensors have dis-aligned field of views (FOVs) in relation to each other, and
      wherein some structured light projectors from said one or more structured light projectors have dis-aligned field of views (FOVs) in relation to each other.

2. The IOS according to claim 1, further comprising one or more light emitters.

3. The IOS according to claim 1, wherein said one or more interconnected boards includes at least one of a staggered rigid PCB, a planar PCB, and a flexible PCB.

4. The IOS according to claim 1, further comprising at least one spacer configured to generate said dis-aligned FOVs.

5. The IOS according to claim 1, further comprising multiple apertures for imaging by said one or more image sensors, wherein at least two of said multiple apertures are configured for imaging at different focal distances.

6. The IOS according to claim 1, further comprising multiple apertures for projecting by said one or more structured light projectors, wherein at least two of said multiple apertures are configured for projecting at different focal distances.

7. The IOS according to claim 1, further comprising circuitry configured for at least one of processing an image acquired by said one or more image sensors and adjusting at least one image acquisition parameter other than exposure based on said processing.

8. The IOS according to claim 7, wherein:
   said processing comprises analyzing at least one image property of said acquired image and determining adjustment of the at least one image acquisition parameter based on said at least one image, and
   said adjustment comprises at least one of:
   a. selecting and/or activating at least one image sensors;
   b. selecting and/or activating at least one structured light projector;
   c. deselecting and/or deactivating at least one image sensors;
   d. deselecting and/or deactivating at least one structured light projector; and
   e. any combination thereof.

9. The IOS according to claim 7, wherein said adjustment comprises signaling user to change spatial orientation of a head of said IOS.

10. The IOS according to claim 7, wherein said processing includes also estimation of an angle of incidence of a first beam of a first light projector over a region of interest (ROI) and estimation of an angle of incidence of a second beam of a second light projector over said ROI.

11. The IOS according to claim 10, wherein said estimated angle of incidence of said first beam is greater than said estimated angle of incidence of said second beam.

12. The IOS according to claim 7, wherein said processing includes tooth segmentation and locating a ROI on said segmented tooth and wherein said adjustment is based on said segmentation.

13. The IOS according to claim 1, wherein a head of said IOS has a width of less than 3 cm and is mounted on a distal portion of a handle of length between 10 to 40 cm.

14. The IOS according to claim 12, wherein said IOS head has a longitudinal axis at an angle of between 85 to 60 degrees of a proximal portion of said handle.

15. The IOS according to claim 12, wherein said IOS head includes a probe at having a distal portion thereof at an angle of between 85 to 60 degrees to a proximal portion of said handle.

16. The IOS according to claim 7, wherein said circuitry is configured for casting a structured light pattern on a ROI, and adjusting said pattern based on said processing.

17. The IOS according to claim 16, wherein said processing includes an estimation of a contrast of said structure light over said ROI and wherein said adjusting is controlled by said circuitry to improve said contrast.

18. A method for intraoral scanning, comprising:
   a. introducing an intraoral scanner (IOS) head of an IOS according to claim 1 into an oral cavity;
   b. acquiring one or more images of a region of interest (ROI);
   c. processing said acquired ROI images; and
   d. adjusting at least one image acquisition parameter other than exposure based on said processing.

19. The method according to claim 18, further comprising predicting at least one future location and/or spatial orientation of said IOS head based on said processing.

20. The method according to claim 19, further comprising analyzing at least one image property of said one or more acquired images and determining at least one future adjustment of at least one image acquisition parameter based on at least one of said image property and said prediction.

* * * * *